US012600720B2

(12) United States Patent
Atton et al.

(10) Patent No.: US 12,600,720 B2
(45) Date of Patent: Apr. 14, 2026

(54) MODULATORS OF THE INTEGRATED STRESS RESPONSE PATHWAY

(71) Applicant: Evotec International GmbH, Hamburg (DE)

(72) Inventors: Holly Victoria Atton, Oxfordshire (GB); Mohamad Sabbah, Oxfordshire (GB)

(73) Assignee: Evotec International GmbH, Hamburg (DE)

( * ) Notice: Subject to any disclaimer, the term of this patent is extended or adjusted under 35 U.S.C. 154(b) by 335 days.

(21) Appl. No.: 18/033,317

(22) PCT Filed: Oct. 21, 2021

(86) PCT No.: PCT/EP2021/079210

§ 371 (c)(1),
(2) Date: Apr. 21, 2023

(87) PCT Pub. No.: WO2022/084448

PCT Pub. Date: Apr. 28, 2022

(65) Prior Publication Data

US 2023/0382905 A1 Nov. 30, 2023

(30) Foreign Application Priority Data

Oct. 22, 2020 (EP) .................................... 20203309

(51) Int. Cl.
*C07D 471/04* (2006.01)
*C07D 413/04* (2006.01)

(52) U.S. Cl.
CPC ......... *C07D 471/04* (2013.01); *C07D 413/04* (2013.01)

(58) Field of Classification Search
CPC .................................................... C07D 413/04
USPC ......................................................... 514/299
See application file for complete search history.

(56) References Cited

U.S. PATENT DOCUMENTS

2020/0095232 A1 3/2020 Biancofiore et al.

FOREIGN PATENT DOCUMENTS

| | | | |
|---|---|---|---|
| CN | 110730777 | A | 1/2020 |
| IN | 201817046151 | A | 2/2019 |
| JP | 2009-516649 | A | 4/2009 |
| JP | 2019-521111 | A | 7/2019 |
| JP | 2020-532506 | A | 11/2020 |
| JP | 2021-508336 | A | 3/2021 |
| WO | WO-2014/144952 | A2 | 9/2014 |
| WO | WO-2017/193030 | A1 | 11/2017 |
| WO | WO-2017/193034 | A1 | 11/2017 |
| WO | WO-2017/193041 | A1 | 11/2017 |
| WO | WO-2017/193063 | A1 | 11/2017 |
| WO | WO-2017/212423 | A1 | 12/2017 |
| WO | WO-2017/212425 | A1 | 12/2017 |
| WO | WO-2018/115275 | A1 | 6/2018 |
| WO | WO-2018/225093 | A1 | 12/2018 |
| WO | WO-2019/008506 | A1 | 1/2019 |
| WO | WO-2019/008507 | A1 | 1/2019 |
| WO | WO-2019/032743 | A1 | 2/2019 |
| WO | WO 2019/046779 | A1 | 3/2019 |
| WO | WO-2019/090069 | A1 | 5/2019 |
| WO | WO-2019/090074 | A1 | 5/2019 |
| WO | WO-2019/090076 | A1 | 5/2019 |
| WO | WO-2019/090078 | A1 | 5/2019 |
| WO | WO-2019/090081 | A1 | 5/2019 |
| WO | WO-2019/090082 | A1 | 5/2019 |

(Continued)

OTHER PUBLICATIONS

Alelyunas, et.al., "Experimental solubility profiling of marketed CNS drugs, exploring solubility limit of CNS discovery candidate," Bioorg. Med. Chem. Lett., 20(24), pp. 7312-7316 (2010).
Avivar-Valderas et al., "Perk Integrates Autophagy and Oxidative Stress Response to Promote Survival during Extracellular Matrix Detachment", Molecular and Cellular Biology 31(17):3616-3629 (2011).
Bi et al., "ER stress-regulated translation increases tolerance to extreme hypoxia and promotes tumor growth", The EMBO Journal 24:3470-3481 (2005).
Blais et al., "Perk-Dependent Translational Regulation Promotes Tumor Cell Adaptation and Angiogenesis in Response to Hypoxic Stress", Molecular and Cellular Biology 26(24):9517-9532 (2006).
Bobrovnikova-Marjon et al., "Perk promotes cancer cell proliferation and tumor growth by limiting oxidative DNA damage", Oncogene 29:3881-3895 (2010).

(Continued)

*Primary Examiner* — Taofiq A Solola
(74) *Attorney, Agent, or Firm* — Foley & Lardner LLP

(57) ABSTRACT

The present invention relates to compounds of formula (I) or pharmaceutically acceptable salts, solvates, hydrates, tautomers or stereoisomers thereof, wherein $R^1$, $R^2$, $R^{2a}$, $R^3$, $R^4$, $R^{4a}$, $R^{4b}$, $R^{4c}$, $R^{4d}$, $R^{4e}$, $R^5$, $R^6$ have the meaning as indicated in the description and claims. The invention further relates to pharmaceutical compositions comprising said compounds, their use as medicament and in a method for treating or preventing of one or more diseases or disorders associated with integrated stress response.

(I)

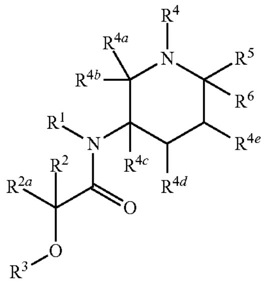

18 Claims, No Drawings

(56) References Cited

FOREIGN PATENT DOCUMENTS

| | | | |
|---|---|---|---|
| WO | WO-2019/090085 | A1 | 5/2019 |
| WO | WO-2019/090088 | A1 | 5/2019 |
| WO | WO-2019/090090 | A1 | 5/2019 |
| WO | WO-2019/118785 | A2 | 6/2019 |
| WO | WO-2019/183589 | A1 | 9/2019 |
| WO | WO-2019/193540 | A1 | 10/2019 |
| WO | WO-2019/193541 | A1 | 10/2019 |
| WO | WO-2019/236710 | A1 | 12/2019 |
| WO | WO-2020/012339 | A1 | 1/2020 |
| WO | WO-2020/031107 | A1 | 2/2020 |
| WO | WO-2020/077217 | A1 | 4/2020 |
| WO | WO-2020/167994 | A1 | 8/2020 |
| WO | WO-2020/168011 | A1 | 8/2020 |
| WO | WO-2020/176428 | A1 | 9/2020 |
| WO | WO-2020/181247 | A1 | 9/2020 |
| WO | WO-2020/216764 | A1 | 10/2020 |
| WO | WO-2020/216766 | A1 | 10/2020 |
| WO | WO-2020/223536 | A1 | 11/2020 |
| WO | WO 2020/223538 | A1 | 11/2020 |
| WO | WO-2020/252205 | A1 | 12/2020 |
| WO | WO-2020/252207 | A1 | 12/2020 |
| WO | WO-2021/151865 | A1 | 8/2021 |
| WO | WO-2021/180774 | A1 | 9/2021 |
| WO | WO-2022/084446 | A1 | 4/2022 |

OTHER PUBLICATIONS

Bugiani et al., "Vanishing white matter: a leukodystrophy due to astrocytic dysfunction", Brain Pathology 28: 408-421 (2018).
Donnelly et al., "The eIF2a kinases: their structures and functions", Cellular and Molecular Life Sciences 70:3493-3511 (2013).
Halliday et al., "Partial restoration of protein synthesis rates by the small molecule ISRIB prevents neurodegeneration without pancreatic toxicity", Cell Death and Disease 6: e1672 (2015).
Halliday et al., "Review: Modulating the unfolded protein response to prevent neurodegeneration and enhance memory", Neuropathology and Applied Neurobiology 41:414-427 (2015).
Hamilton et al., "Natural History of Vanishing White Matter", Ann Neurol. 84:274-288 (2018).
Hinnebusch et al., "Translational control by 5'-untranslated regions of eukaryotic mRNAs", Science 352(6292): 1413-1416 (2016).
Jackson et al., "The mechanism of eukaryotic translation initiation and principles of its regulation", Nature Reviews: Molecular Cell Biology 10: 113-127 (2010).
Krishnamoorthy et al., "Tight Binding of the Phosphorylated a Subunit of Initiation Factor 2 (eIF2a) to the Regulatory Subunits of Guanine Nucleotide Exchange Factor eIF2B Is Required for Inhibition of Translation Initiation", Molecular and Cellular Biology 21(15): 5018-5030 (2001).
Lin et al., "Divergent Effects of Perk and IRE1 Signaling on Cell Viability", PLoS One 4(1): 1-4 (2009).
Lomakin et al., "The initiation of mammalian protein synthesis and mRNA scanning mechanism", Nature 500: 307-311 (2013).
Moreno et al., "Sustained translational repression by eIF2a-P mediates prion neurodegeneration", Nature 485: 507-511 (2012).
Nguyen et al., "Development of a stress response therapy targeting aggressive prostate cancer", Science Translational Medicine 10, eaar2036, 11 pages (2018).
Pain, "Initiation of protein synthesis in eukaryotic cells", Eur. J. Biochem 236: 747-771 (1996).
Pakos-Zebrucka et al., "The integrated stress response," EMBO Reports 17, pp. 1374-1395 (2016).
Pavitt, "Regulation of translation initiation factor eIF2B at the hub of the integrated stress response", Wires RNA 9:e1491 (2018).
Redfern, et.al., "Relationships between preclinical cardiac electrophysiology, clinical QT interval prolongation and torsade de pointes for a broad range of drugs," Cardiovascular Research 58, pp. 32-45 (2003).
Remondelli et al., "The Endoplasmic Reticulum Unfolded Protein Response in Neurodegenerative Disorders and Its Potential Therapeutic Significance", Frontiers in Molecular Neuroscience 10(187): 1-16 (2017).
Shore et al., "Signaling cell death from the endoplasmic reticulum stress response", Current Opinion in Cell Biology 23: 143-149 (2011).
Skopkova et al., "EIF2S3 Mutations Associated with Severe X-Linked Intellectual Disability Syndrome MEHMO", Human Mutation 38(4): 409-425 (2017).
Taalab et al., "Mechanisms of disordered neurodegenerative function: concepts and facts about the different roles of the protein kinase RNA-like endoplasmic reticulum kinase (PERK)", Rev. Neurosci. 29(4): 387-415 (2018).
Tabas et al., "Integrating the mechanisms of apoptosis induced by endoplasmic reticulum stress", Nature Cell Biology 13(3): 184-190 (2011).
Waring, "Lipophilicity in Drug Discovery," Expert Opinion on Drug Discovery, vol. 5,—Issue 3, pp. 235-248 (2010).
Wek et al., "Coping with stress: eIF2 kinases and translational control", Biochemical Society Transactions 34(1): 7-11 (2006).
Wong et al., "eIF2B activator prevents neurological defects caused by a chronic integrated stress response", eLife (2019), 31 pages.
Wong et al., "The small molecule ISRIB rescues the stability and activity of Vanishing White Matter Disease eIF2B mutant complexes", eLife 7: e32733 (2018).
Young et al., "Upstream open reading frames differentially regulate gene-specific translation in the integrated stress response", The Journal of Biological Chemistry, 291(33): 16927-16935 (2016).
International Search Report and Written Opinion issued in International Patent Application No. PCT/EP2021/079210, dated Jan. 7, 2022.
Notice for Reasons for Rejection issued in Japanese Patent Application No. 2023-524307, dated Oct. 21, 2025 (9 pages).
CN Office Action on CN Appl. No. 202180086791.2 dated Jul. 9, 2025 (11 pages with English language translation).

MODULATORS OF THE INTEGRATED STRESS RESPONSE PATHWAY

CROSS-REFERENCE TO RELATED APPLICATIONS

This application is the U.S. National Stage of International Patent Application No. PCT/EP2021/079210, filed Oct. 21, 2021, which claims priority from European Patent Application No. 20203309.8, filed Oct. 22, 2020. The contents of these applications are incorporated herein by reference in their entirety.

The present invention relates to compounds of formula (I)

(I)

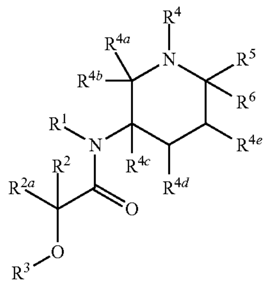

or pharmaceutically acceptable salts, solvates, hydrates, tautomers or stereoisomers thereof, wherein $R^1$, $R^2$, $R^{2a}$, $R^3$, $R^4$, $R^{4a}$, $R^{4b}$, $R^{4c}$, $R^{4d}$, $R^{4e}$, $R^5$, $R^6$ have the meaning as indicated in the description and claims. The invention further relates to pharmaceutical compositions comprising said compounds, their use as medicament and in a method for treating or preventing of one or more diseases or disorders associated with integrated stress response.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-tRNA$_i$ forming a ternary complex (eIF2-GTP-Met-tRNA$_i$), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed PERK$^{-/-}$ mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eTF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

Modulators of the eIF2 alpha pathway are described in WO 2014/144952 A2. WO 2017/193030 A1, WO 2017/193034 A1, WO 2017/193041 A1 and WO 2017/193063 A1 describe modulators of the integrated stress pathway. WO 2017/212423 A1, WO 2017/212425 A1, WO 2018/225093 A1, WO 2019/008506 A1 and WO 2019/008507 A1 describe inhibitors of the ATF4 pathway. WO 2019/032743 A1, WO 2019/046779 A1, WO 2020/167994 A1, WO 2020/168011 A1 and WO 2020/181247 A1 relate to eukaryotic initiation factor 2B modulators. In WO 2020/77217 A1 compounds, compositions, and methods useful for modulating the integrated stress response (ISR) and for treating related diseases, disorders and conditions are described.

Further documents describing modulators of the integrated stress pathway are WO 2019/090069 A1, WO 2019/090074 A1, WO 2019/090076 A1, WO 2019/090078 A1, WO 2019/090081 A1, WO 2019/090082 A1, WO 2019/090085 A1, WO 2019/090088 A1, WO 2019/090090 A1, WO 2020/223536 A1, WO 2020/223538 A1, WO 2020/252207 A1, WO 2020/252205 A1, European patent applications 20203312.2, 20203311.4 and 21192154.9, WO 2021/180774 A1, WO 2021/151865 A1, WO 2020/216764 A1 and WO 2020/216766 A1.

Modulators of eukaryotic initiation factors are described in WO 2019/183589 A1. WO 2019/118785 A2, WO 2019/236710 A1 and WO 2020/176428 A1 describe inhibitors of the integrated stress response pathway. Heteroaryl derivatives as ATF4 inhibitors are described in WO 2019/193540 A1. Bicyclic aromatic ring derivatives as ATF4 inhibitors are described in WO 2019/193541 A1. WO 2020/031107 A1 and WO 2020/012339 A1 describe inhibitors of the ATF4 pathway.

However, there is a continuing need for new compounds useful as modulators of the integrated stress response pathway with good pharmacokinetic properties.

Thus, an object of the present invention is to provide a new class of compounds as modulators of the integrated stress response pathway, which may be effective in the treatment of integrated stress response pathway related diseases and which may show improved pharmaceutically relevant properties including activity, solubility, selectivity, ADMET properties and/or reduced side effects.

Accordingly, the present invention provides a compound of formula (I)

(I)

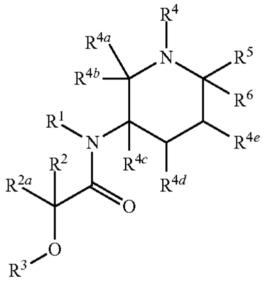

or a pharmaceutically acceptable salt, solvate, hydrate, tautomer or stereoisomer thereof, wherein $R^1$ is H or $C_{1-4}$ alkyl, preferably H, wherein $C_{1-4}$ alkyl is optionally substituted with one or more halogen, which are the same or different;

$R^2$ is H, F or $C_{1-4}$ alkyl, wherein $C_{1-4}$ alkyl is optionally substituted with one or more halogen, which are the same or different;

$R^{2a}$ is H or F, preferably H;

$R^3$ is phenyl or 6 membered aromatic heterocyclyl, wherein $R^3$ is optionally substituted with one or more $R^7$, which are the same or different;

$R^7$ is halogen, CN, $C(O)OR^8$, $OR^8$, $C(O)R^8$, $C(O)N(R^8R^{8a})$, $S(O)_2N(R^8R^{8a})$, $S(O)N(R^8R^{8a})$, $S(O)_2R^8$, $S(O)R^8$, $N(R^8)S(O)_2N(R^{8a}R^{8b})$, $SR^8$, $N(R^8R^{8a})$, $NO_2$, $OC(O)R^8$, $N(R^8)C(O)R^{8a}$, $N(R^8)S(O)_2R^{8a}$, $N(R^8)S(O)R^{8a}$, $N(R^8)C(O)OR^{8a}$, $N(R^8)C(O)N(R^{8a}R^{8b})$, $OC(O)N(R^8R^{8a})$, $C_{1-6}$ alkyl, $C_{2-6}$ alkenyl or $C_{2-6}$ alkynyl, wherein $C_{1-6}$ alkyl, $C_{2-6}$ alkenyl and $C_{2-6}$ alkynyl are optionally substituted with one or more $R^9$, which are the same or different;

$R^8$, $R^{8a}$, $R^{8b}$ are independently selected from the group consisting of H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl are optionally substituted with one or more halogen, which are the same or different;

$R^9$ is halogen, CN, $C(O)OR^{10}$, $OR^{10}$, $C(O)R^{10}$, $C(O)N(R^{10}R^{10a})$, $S(O)_2N(R^{10}R^{10a})$, $S(O)N(R^{10}R^{10a})$, $S(O)_2R^{10}$, $S(O)R^{10}$, $N(R^{10})S(O)_2N(R^{10a}R^{10b})$, $SR^{10}$, $N(R^{10}R^{10a})$, $NO_2$, $OC(O)R^{10}$, $N(R^{10})C(O)R^{10a}$, $N(R^{10})SO_2R^{10a}$, $N(R^{10})S(O)R^{10a}$, $N(R^{10})C(O)N(R^{10a}R^{10b})$, $N(R^{10})C(O)OR^{10a}$ or $OC(O)N(R^{10}R^{10a})$;

$R^{10}$, $R^{10a}$, $R^{10b}$ are independently selected from the group consisting of H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl are optionally substituted with one or more halogen, which are the same or different.

$R^4$ is H, $C(O)OC_{1-4}$ alkyl or $C_{1-4}$ alkyl, wherein $C(O)OC_{1-4}$ alkyl and $C_{1-4}$ alkyl are optionally substituted with one or more substituents selected from the group consisting of halogen, OH and O—$C_{1-3}$ alkyl, wherein the substituents are the same or different;

$R^{4a}$, $R^{4b}$, $R^{4c}$, $R^5$ are independently selected from the group consisting of H, halogen and $C_{1-4}$ alkyl; and $R^{4d}$, $R^{4e}$ are independently selected from the group consisting of H, OH, $OC_{1-4}$ alkyl, halogen and $C_{1-4}$ alkyl;

or $R^4$ and one of $R^{4d}$ and $R^{4e}$ form a methylene or ethylene group;

or $R^4$ and $R^{4c}$ form an ethylene group;

or $R^{4b}$ and $R^{4d}$ form a covalent single bond;

$R^6$ is 7 to 12 membered heterobicyclyl, wherein $R^6$ is optionally substituted with one or more $R^{11}$, which are the same or different;

$R^{11}$ is $R^{12}$, OH, $OR^{12}$, halogen or CN, and $R^{12}$ is cyclopropyl, $C_{1-6}$ alkyl, $C_{2-6}$ alkenyl or $C_{2-6}$ alkynyl, wherein $R^{12}$ is optionally substituted with one or more $R^{13}$, which are the same or different;

$R^{13}$ is halogen, CN or $OR^{14}$;

$R^{14}$ is H or $C_{1-4}$ alkyl, wherein $C_{1-4}$ alkyl is optionally substituted with one or more halogen, which are the same or different.

Surprisingly, the disclosed example compounds according to the present invention have favourable physico-chemical properties and/or selectivity, which combine to help to achieve beneficial therapeutic efficacy whilst limiting unintended liabilities.

In case a variable or substituent can be selected from a group of different variants and such variable or substituent occurs more than once the respective variants can be the same or different.

Within the meaning of the present invention the terms are used as follows:

The term "optionally substituted" means unsubstituted or substituted. Generally—but not limited to—, "one or more substituents" means one, two or three, preferably one or two substituents and more preferably one substituent. Generally these substituents can be the same or different. The term "one or more substituents" also means by way of example one, two, three, four or five, preferably by way of example one, two, three or four.

"Alkyl" means a straight-chain or branched hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. $—CH_2—$, $—CH_2—CH_2—$, $—CH(CH_3)—$, $—CH_2—CH_2—CH_2—$, $—CH(C_2H_5)—$, $—C(CH_3)_2—$, when two moieties of a molecule are linked by the alkyl group. Each hydrogen of a $C_{1-4}$ alkyl carbon may be replaced by a substituent as further specified. The term "$C_{1-3}$ alkyl" is defined accordingly.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. $—CH_2—$, $—CH_2—CH_2—$, $—CH(CH_3)—$, $—CH_2—CH_2—CH_2—$, $—CH(C_2H_5)—$, $—C(CH_3)_2—$, when two moieties of a molecule are linked by the alkyl group. Each hydrogen of a $C_{1-6}$ alkyl carbon may be replaced by a substituent as further specified.

"$C_{2-6}$ alkenyl" means an alkenyl chain having 2 to 6 carbon atoms, e.g. if present at the end of a molecule: $—CH=CH_2$, $—CH=CH—CH_3$, $—CH_2—CH=CH_2$, $—CH=CH—CH_2—CH_3$, $—CH=CH—CH=CH_2$, or e.g. $—CH=CH—$, when two moieties of a molecule are linked by the alkenyl group. Each hydrogen of a $C_{2-6}$ alkenyl carbon may be replaced by a substituent as further specified.

"$C_{2-6}$ alkynyl" means an alkynyl chain having 2 to 6 carbon atoms, e.g. if present at the end of a molecule: $—C≡CH$, $—CH_2—C≡CH$, $CH_2—CH_2—C≡CH$, $CH_2—C≡C—CH_3$, or e.g. $—C≡C—$ when two moieties of a molecule are linked by the alkynyl group. Each hydrogen of a $C_{2-6}$ alkynyl carbon may be replaced by a substituent as further specified.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cycloalkyl refers to cyclopropyl, cyclobutyl, cyclopentyl, cyclohexyl, or cycloheptyl. Each hydrogen of a cycloalkyl carbon may be replaced by a substituent as further specified herein. The term "$C_{3-5}$ cycloalkyl" or "$C_{3-5}$ cycloalkyl ring" is defined accordingly.

"$C_5$ cycloalkylene" refers to a bivalent cycloalkyl with five carbon atoms, i.e. a bivalent cyclopentyl ring.

"$C_5$ cycloalkenylene" refers to a bivalent cycloalkenylene, i.e. a bivalent cyclopentene or cyclopentadiene.

"$C_{4-12}$ bicycloalkyl" or "$C_{4-12}$ bicycloalkyl ring" means a bicyclic fused, bridged or spiro alkyl chain having 4 to 12 carbon atoms, e.g. hexahydroindane, Octahydropentalen, bicycle[2.2.1]heptane or spiro(3.2)hexane. Each hydrogen of a bicycloalkyl carbon may be replaced by a substituent as further specified herein.

"Halogen" means fluoro, chloro, bromo or iodo. It is generally preferred that halogen is fluoro or chloro.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including $—S(O)—$, $—S(O)_2—$), oxygen and nitrogen (including $=N(O)—$) and wherein the ring is linked to the rest of the molecule via a carbon or nitrogen atom. Examples for a 3 to 7 membered heterocycle are aziridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly and and includes 5 to 6 membered aromatic heterocyclyl or heterocycle. The term "5 membered heterocyclyl" or "5 membered heterocycle" is defined accordingly and includes 5 membered aromatic heterocyclyl or heterocycle.

The term "nitrogen ring atom containing 5-membered heterocyclene" refers to a bivalent 5-membered heterocycle, wherein at least one of the five ring atoms is a nitrogen atom and wherein the ring is linked to the rest of the molecule via a carbon or nitrogen atom.

"Saturated 4 to 7 membered heterocyclyl" or "saturated 4 to 7 membered heterocycle" means fully saturated "4 to 7 membered heterocyclyl" or "4 to 7 membered heterocycle".

"4 to 7 membered at least partly saturated heterocyclyl" or "4 to 7 membered at least partly saturated heterocycle" means an at least partly saturated "4 to 7 membered heterocyclyl" or "4 to 7 membered heterocycle".

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including $—S(O)—$, $—S(O)_2—$), oxygen and nitrogen (including $=N(O)—$). Examples for such heterocycles are furan, thiophene, pyrrole, imidazole, pyrazole, oxazole, isoxazole, thiazole, isothiazole, thiadiazole, triazole, tetrazole, pyridine, pyrimidine, pyridazine, pyrazine, triazine.

"5 membered aromatic heterocyclyl" or "5 membered aromatic heterocycle" means a heterocycle derived from cyclopentadienyl, where at least one carbon atom is replaced by a heteroatom selected from the group consisting of sulfur (including $—S(O)—$, $—S(O)_2—$), oxygen and nitrogen (including $=N(O)—$). Examples for such heterocycles are furan, thiophene, pyrrole, imidazole, pyrazole, oxazole, isoxazole, thiazole, isothiazole, thiadiazole, triazole, tetrazole.

"6 membered aromatic heterocyclyl" or "6 membered aromatic heterocycle" means a heterocycle derived from benzene, where at least one carbon atom is replaced by a heteroatom selected from the group consisting of sulfur (including $—S(O)—$, $—S(O)_2—$), oxygen and nitrogen (including $=N(O)—$). Examples for such heterocycles are pyridine, pyrimidine, pyridazine, pyrazine, triazine.

"7 to 12 membered heterobicyclyl" or "7 to 12 membered heterobicycle" means a heterocyclic system of two rings with 7 to 12 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for a 7 to 12 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 12 membered heterobicycle also includes spiro structures of two rings like 6-oxa-2-azaspiro[3,4]octane, 2-oxa-6-azaspiro[3.3]heptan-6-yl or 2,6-diazaspiro[3.3]heptan-6-yl or bridged heterocycles like 8-aza-bicyclo[3.2.1]octane or 2,5-diazabicyclo[2.2.2]octan-2-yl or 3,8-diazabicyclo[3.2.1]octane.

"Saturated 7 to 12 membered heterobicyclyl" or "saturated 7 to 12 membered heterobicycle" means fully saturated "7 to 12 membered heterobicyclyl" or "7 to 12 membered heterobicycle".

"7 to 12 membered at least partly saturated heterobicyclyl" or "7 to 12 membered at least partly saturated heterobicycle" means an at least partly saturated "7 to 12 membered heterobicyclyl" or "7 to 12 membered heterobicycle".

"9 to 11 membered aromatic heterobicyclyl" or "9 to 11 membered aromatic heterobicycle" means a heterocyclic system of two rings, wherein at least one ring is aromatic and wherein the heterocyclic ring system has 9 to 11 ring atoms, where two ring atoms are shared by both rings and that may contain up to the maximum number of double bonds (fully or partially aromatic) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for an 9 to 11 membered aromatic heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, isoquinoline, tetrahydroisoquinoline, dihydroisoquinoline, benzazepine, purine or pteridine. The terms "9 to 10 membered aromatic heterobicyclyl" or "9 to 10 membered aromatic heterobicycle" are defined accordingly.

Preferred compounds of formula (I) are those compounds in which one or more of the residues contained therein have the meanings given above or below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, $R^4$ is H, $CH_3$, $CH_2CH_3$, or $CH_2CH_2OCH_3$; more preferably, H or $CH_3$; even more preferably H.

Preferably, $R^{4a}$, $R^{4b}$, $R^{4c}$, $R^5$ are independently selected from the group consisting of H, halogen and $C_{1-4}$ alkyl and $R^{4d}$, $R^{4e}$ are independently selected from the group consisting of H, OH, $OC_{1-4}$ alkyl, halogen and $C_{1-4}$ alkyl; more preferably $R^{4a}$, $R^{4b}$, $R^{4c}$, $R^5$, $R^{4d}$, $R^{4e}$ are independently selected from the group consisting of H, F and $CH_3$; even more preferably $R^{4a}$, $R^{4b}$, $R^{4c}$, $R^5$, $R^{4d}$, $R^{4e}$ are H.

Preferably, $R^1$ is H or $CH_3$; more preferably H.

Preferably, $R^2$ is H, F or $CH_3$, more preferably H.

Preferably, $R^1$, $R^2$, $R^{2a}$, $R^4$, $R^{4a}$, $R^{4b}$, $R^{4c}$, $R^5$, $R^{4d}$, $R^{4e}$, in formula (I) are H to give formula (Ia)

(Ia)

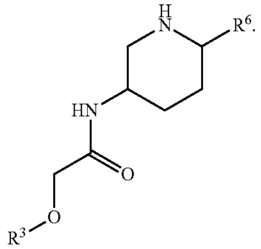

Preferably, $R^3$ is phenyl or pyridyl, preferably phenyl, wherein $R^3$ is optionally substituted with one or more $R^7$, which are the same or different.

Preferably, $R^3$ is substituted with one, two or three, preferably one or two, more preferably two, $R^7$, which are the same or different.

Preferably, $R^9$ is halogen.

Preferably, $R^7$ is F, Cl, Br, CN, $CHF_2$, $CF_3$, $OCH_3$, $OCF_3$, CH=O, $CH_2OH$ or $CH_3$; more preferably $R^7$ is $CF_3$, F or Cl; even more preferably F or Cl.

Preferably, $R^1$, $R^2$, $R^{2a}$, $R^3$, $R^4$, $R^{4a}$, $R^{4b}$, $R^{4c}$, $R^{4d}$, $R^{4e}$, $R^5$ in formula (I) are selected to give formula (Ib)

(Ib)

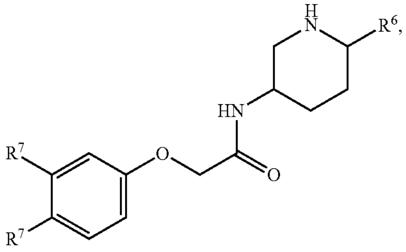

wherein each $R^7$ is independently selected from the group consisting of halogen and $CF_3$.

Preferably, $R^7$ groups are selected in formula (Ib) to give formula (Ib1)

(Ib1)

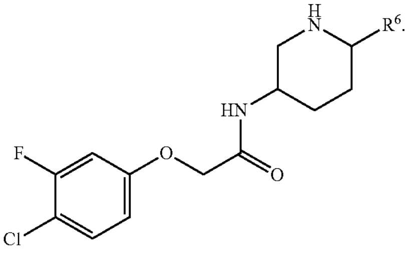

Preferably, $R^6$ is quinazolinyl, pyrrolo[1,2-a]pyrazinyl, 1,3-benzoxazolyl, pyrido[2,3-d]pyrimidinyl, pyrido[3,4-d]pyrimidinyl, pyrimido[5,4-d]pyrimidinyl, 1,2,3,4-tetrahydroquinolinyl, chromanyl, oxazolo[4,5-c]pyridinyl, imidazo[1,2-a]pyridinyl, [1,2,4]triazolo[1,5-a]pyridinyl, imidazo[1,2-b]pyridazinyl or 6,7-dihydro-4H-pyrano[4,3-d]oxazolyl, wherein $R^6$ is optionally substituted with one or more $R^{11}$, which are the same or different. More preferably, $R^6$ is 1,3-benzoxazolyl or imidazo[1,2-a]pyridinyl, wherein $R^6$ is optionally substituted with one or more $R^{11}$, which are the same or different. Even more preferably, $R^6$ is 1,3-benzoxazolyl, wherein $R^6$ is optionally substituted with one or more $R^{11}$, which are the same or different.

Preferably, $R^6$ is unsubstituted or substituted with one or two $R^{11}$, which are the same or different.

Preferably, $R^{11}$ is Cl, $CH_3$, $CF_3$, $CH_2CF_3$, $OCF_3$, $OCHF_2$ or $OCH_2CF_3$. Preferably, $R^{11}$ is Cl, $CH_3$, $CF_3$, $CH_2CF_3$, $OCF_3$ or $OCH_2CF_3$.

Compounds of the formula (I) in which some or all of the above-mentioned groups have the preferred or more preferred meanings are also an object of the present invention.

For preferred specific compounds or pharmaceutically acceptable salts, solvates, hydrates, tautomers or stereoisomers thereof of the present invention $R^1$, $R^2$, $R^{2a}$, $R^3$, $R^4$, $R^{4a}$, $R^{4b}$, $R^{4c}$, $R^{4d}$, $R^{4e}$, $R^5$, $R^6$ in formula (I) are selected to give tert-butyl (2R,5S)-2-(6-chloro-1,3-benzoxazol-2-yl)-5-[2-(4-chloro-3-fluorophenoxy)acetamido]piperidine-1-carboxylate;

N-[(3S,6R)-6-(6-chloro-1,3-benzoxazol-2-yl)piperidin-3-yl]-2-(4-chloro-3-fluorophenoxy)acetamide;

tert-butyl (2R,5S)-2-(5-chloro-1,3-benzoxazol-2-yl)-5-[2-(4-chloro-3-fluorophenoxy)acetamido]piperidine-1-carboxylate;

N-[(3S,6R)-6-(5-chloro-1,3-benzoxazol-2-yl)piperidin-3-yl]-2-(4-chloro-3-fluorophenoxy)acetamide;

tert-butyl (2R,5S)-5-[[2-(4-chloro-3-fluoro-phenoxy)acetyl]amino]-2-[6-(trifluoromethyl)imidazo[1,2-a]pyridin-2-yl]piperidine-1-carboxylate;

2-(4-chloro-3-fluoro-phenoxy)-N-[(3S,6R)-6-[6-(trifluoromethyl)imidazo[1,2-a]pyridin-2-yl]-3-piperidyl]acetamide;

tert-butyl (2R,5S)-5-[2-(4-chloro-3-fluorophenoxy)acetamido]-2-[7-(trifluoromethyl)imidazo[1,2-a]pyridin-2-yl]piperidine-1-carboxylate;

2-(4-chloro-3-fluoro-phenoxy)-N-[(3S,6R)-6-[7-(trifluoromethyl)imidazo[1,2-a]pyridin-2-yl]-3-piperidyl]acetamide;

tert-butyl (2R,5S)-2-(7-chloro-1,3-benzoxazol-2-yl)-5-[2-(4-chloro-3-fluorophenoxy)acetamido]piperidine-1-carboxylate;

N-[(3S,6R)-6-(7-chloro-1,3-benzoxazol-2-yl)piperidin-3-yl]-2-(4-chloro-3-fluorophenoxy)acetamide;

tert-butyl (2R,5S)-5-[2-(4-chloro-3-fluorophenoxy)acetamido]-2-[6-(trifluoromethoxy)-1,3-benzoxazol-2-yl]piperidine-1-carboxylate;

2-(4-chloro-3-fluorophenoxy)-N-[(3S,6R)-6-[6-(trifluoromethoxy)-1,3-benzoxazol-2-yl]piperidin-3-yl]acetamide;

tert-butyl (2R,5S)-5-[2-(4-chloro-3-fluorophenoxy)acetamido]-2-[6-(difluoromethoxy)-1,3-benzoxazol-2-yl]piperidine-1-carboxylate;

2-(4-chloro-3-fluorophenoxy)-N-[(3S,6R)-6-[6-(difluoromethoxy)-1,3-benzoxazol-2-yl]piperidin-3-yl]acetamide;

tert-butyl (2R,5S)-5-[2-(4-chloro-3-fluorophenoxy)acetamido]-2-[6-(trifluoromethyl)-1,3-benzoxazol-2-yl]piperidine-1-carboxylate;

2-(4-chloro-3-fluorophenoxy)-N-[(3S,6R)-6-[6-(trifluoromethyl)-1,3-benzoxazol-2-yl]piperidin-3-yl]acetamide;

tert-butyl (2R,5S)-2-(4-chloro-1,3-benzoxazol-2-yl)-5-[2-(4-chloro-3-fluorophenoxy)acetamido]piperidine-1-carboxylate; or N-[(3S,6R)-6-(4-chloro-1,3-benzoxazol-2-yl)piperidin-3-yl]-2-(4-chloro-3-fluorophenoxy)acetamide.

Where tautomerism, like e.g. keto-enol tautomerism, of compounds of formula (I) may occur, the individual forms, like e.g. the keto and enol form, are comprised separately and together as mixtures in any ratio. Same applies to stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

A preferred compound is a compound or a pharmaceutically acceptable salt, solvate, hydrate, tautomer or stereoisomer thereof of formula (I) with a relative configuration as shown in formula (Ic)

(Ic)

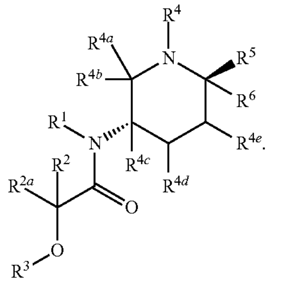

Isotopic labeled compounds of formula (I) are also within the scope of the present invention. Methods for isotope labeling are known in the art. Preferred isotopes are those of the elements H, C, N, O and S. Solvates and hydrates of compounds of formula (I) are also within the scope of the present invention.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

As shown below compounds of the present invention are believed to be suitable for modulating the integrated stress response pathway.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-$tRNA_i$ forming a ternary complex (eIF2-GTP-Met-$tRNA_i$), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed $PERK^{-/-}$ mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eTF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

The present invention provides compounds of the present invention in free or pharmaceutically acceptable salt form or in the form of solvates, hydrates, tautomers or stereoisomers to be used in the treatment of diseases or disorders mentioned herein. The same applies to a pharmaceutical composition of the present invention.

Thus an aspect of the present invention is a compound or a pharmaceutically acceptable salt, solvate, hydrate, tautomer or stereoisomer thereof of the present invention for use as a medicament. The same applies to a pharmaceutical composition of the present invention.

The therapeutic method described may be applied to mammals such as dogs, cats, cows, horses, rabbits, monkeys and humans. Preferably, the mammalian patient is a human patient.

Accordingly, the present invention provides a compound or a pharmaceutically acceptable salt, solvate, hydrate, tautomer or stereoisomer thereof or a pharmaceutical composition of the present invention to be used in the treatment or prevention of one or more diseases or disorders associated with integrated stress response.

A further aspect of the present invention is a compound or a pharmaceutically acceptable salt, solvate, hydrate, tautomer or stereoisomer thereof or a pharmaceutical composition of the present invention for use in a method of treating or preventing one or more disorders or diseases associated with integrated stress response.

A further aspect of the present invention is the use of a compound or a pharmaceutically acceptable salt, solvate, hydrate, tautomer or stereoisomer thereof or a pharmaceutical composition of the present invention for the manufacture of a medicament for the treatment or prophylaxis of one or more disorders or diseases associated with integrated stress response.

Yet another aspect of the present invention is a method for treating, controlling, delaying or preventing in a mammalian patient in need of the treatment of one or more diseases or disorders associated with integrated stress response, wherein the method comprises administering to said patient a therapeutically effective amount of a compound or a pharmaceutically acceptable salt, solvate, hydrate, tautomer or stereoisomer thereof or a pharmaceutical composition of the present invention.

The present invention provides a compound or a pharmaceutically acceptable salt, solvate, hydrate, tautomer or stereoisomer thereof or a pharmaceutical composition of the present invention to be used in the treatment or prevention of one or more diseases or disorders mentioned below.

A further aspect of the present invention is a compound or a pharmaceutically acceptable salt, solvate, hydrate, tautomer or stereoisomer thereof or a pharmaceutical composition of the present invention for use in a method of treating or preventing one or more disorders or diseases mentioned below.

A further aspect of the present invention is the use of a compound or a pharmaceutically acceptable salt, solvate, hydrate, tautomer or stereoisomer thereof or a pharmaceutical composition of the present invention for the manufacture of a medicament for the treatment or prophylaxis of one or more disorders or diseases mentioned below.

Yet another aspect of the present invention is a method for treating, controlling, delaying or preventing in a mammalian patient in need of the treatment of one or more diseases or disorders mentioned below, wherein the method comprises administering to said patient a therapeutically effective amount of a compound or a pharmaceutically acceptable salt, solvate, hydrate, tautomer or stereoisomer thereof or a pharmaceutical composition of the present invention.

Diseases or disorders include but are not limited to leukodystrophies, intellectual disability syndrome, neurodegenerative diseases and disorders, neoplastic diseases, infectious diseases, inflammatory diseases, musculoskeletal diseases, metabolic diseases, ocular diseases as well as diseases selected from the group consisting of organ fibrosis, chronic and acute diseases of the liver, chronic and acute diseases of the lung, chronic and acute diseases of the kidney, myocardial infarction, cardiovascular disease, arrhythmias, atherosclerosis, spinal cord injury, ischemic stroke, and neuropathic pain.

Leukodystrophies

Examples of leukodystrophies include, but are not limited to, Vanishing White Matter Disease (VWMD) and childhood ataxia with CNS hypo-myelination (e.g. associated with impaired function of eIF2 or components in a signal transduction or signaling pathway including eIF2).

Intellectual Disability Syndrome

Intellectual disability in particular refers to a condition in which a person has certain limitations in intellectual functions like communicating, taking care of him- or herself, and/or has impaired social skills. Intellectual disability syndromes include, but are not limited to, intellectual disability conditions associated with impaired function of eIF2 or components in a signal transduction or signaling pathway including eIF2.

Neurodegenerative Diseases/Disorders

Examples of neurodegenerative diseases and disorders include, but are not limited to, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Progressive supranuclear palsy, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, and tauopathies.

In particular, the neurodegenerative disease or and disorder is selected from the group consisting of Alzheimer's disease, Parkinson's disease and amyotrophic lateral sclerosis.

Neoplastic Diseases

A neoplastic disease may be understood in the broadest sense as any tissue resulting from miss-controlled cell growth. In many cases a neoplasm leads to at least bulky tissue mass optionally innervated by blood vessels. It may or may not comprise the formation of one or more metastasis/metastases. A neoplastic disease of the present invention may be any neoplasm as classified by the International Statistical Classification of Diseases and Related Health Problems 10th Revision (ICD-10) classes C00-D48.

Exemplarily, a neoplastic disease according to the present invention may be the presence of one or more malignant neoplasm(s) (tumors) (ICD-10 classes C00-C97), may be the presence of one or more in situ neoplasm(s) (ICD-10 classes D00-D09), may be the presence of one or more benign neoplasm(s) (ICD-10 classes D10-D36), or may be the presence of one or more neoplasm(s) of uncertain or unknown behavior (ICD-10 classes D37-D48). Preferably, a neoplastic disease according to the present invention refers to the presence of one or more malignant neoplasm(s), i.e., is malignant neoplasia (ICD-10 classes C00-C97).

In a more preferred embodiment, the neoplastic disease is cancer.

Cancer may be understood in the broadest sense as any malignant neoplastic disease, i.e., the presence of one or more malignant neoplasm(s) in the patient. Cancer may be solid or hematologic malignancy. Contemplated herein are without limitation leukemia, lymphoma, carcinomas and sarcomas.

In particular, neoplastic diseases, such as cancers, characterized by upregulated ISR markers are included herein.

Exemplary cancers include, but are not limited to, thyroid cancer, cancers of the endocrine system, pancreatic cancer, brain cancer (e.g. glioblastoma multiforme, glioma), breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), cervix cancer, ovarian cancer, uterus cancer, colon cancer, head & neck cancer, liver cancer (e.g. hepatocellular carcinoma), kidney cancer, lung cancer (e.g. non-small cell lung carcinoma, squamous cell lung carcinoma, adenocarcinoma, large cell lung carcinoma, small cell lung carcinoma, carcinoid, sarcoma), colon cancer, esophageal cancer, stomach cancer, bladder cancer, bone cancer, gastric cancer, prostate cancer and skin cancer (e.g. melanoma).

Further examples include, but are not limited to, myeloma, leukemia, mesothelioma, and sarcoma.

Additional examples include, but are not limited to, Medulloblastoma, Hodgkin's Disease, Non-Hodgkin's Lymphoma, multiple myeloma, neuroblastoma, glioma, glioblastoma multiforme, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, and cancer of the hepatic stellate cells.

Exemplary leukemias include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

Exemplary sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Exemplary melanomas include, but are not limited to, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Exemplary carcinomas include, but are not limited to, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, and carcinoma villosum.

Infectious Diseases

Examples include, but are not limited to, infections caused by viruses (such as infections by HIV-1: human immunodeficiency virus type 1; IAV: influenza A virus; HCV: hepatitis C virus; DENV: dengue virus; ASFV: African swine fever virus; EBV: Epstein-Barr virus; HSV1: herpes simplex virus 1; CHIKV: chikungunya virus; HCMV: human cytomegalovirus; SARS-CoV: severe acute respiratory syndrome coronavirus; SARS-CoV-2: severe acute respiratory syndrome coronavirus 2) and infections caused by bacteria (such as infections by *Legionella, Brucella, Simkania, Chlamydia, Helicobacter* and *Campylobacter*).

Inflammatory Diseases

Examples of inflammatory diseases include, but are not limited to, postoperative cognitive dysfunction (decline in cognitive function after surgery), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

Musculoskeletal Diseases

Examples of musculoskeletal diseases include, but are not limited to, muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, and paralysis.

Detabolic Diseases

Examples of metabolic diseases include, but are not limited to, diabetes (in particular diabetes Type II), non-alcoholic steatohepatitis (NASH), non-alcoholic fatty liver disease (NAFLD), Niemann-Pick disease, liver fibrosis, obesity, heart disease, atherosclerosis, arthritis, cystinosis, phenylketonuria, proliferative retinopathy, and Kearns-Sayre disease.

Ocular Diseases

Examples of ocular diseases include, but are not limited to, edema or neovascularization for any occlusive or inflammatory retinal vascular disease, such as rubeosis irides, neovascular glaucoma, pterygium, vascularized glaucoma filtering blebs, conjunctival papilloma; choroidal neovascularization, such as neovascular age-related macular degeneration (AMD), myopia, prior uveitis, trauma, or idiopathic; macular edema, such as post surgical macular edema, macular edema secondary to uveitis including retinal and/or choroidal inflammation, macular edema secondary to diabetes, and macular edema secondary to retinovascular occlusive disease (i.e. branch and central retinal vein occlusion); retinal neovascularization due to diabetes, such as retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease; and genetic disorders, such as VonHippel-Lindau syndrome.

Further Diseases

Further diseases include, but are not limited to, organ fibrosis (such as liver fibrosis, lung fibrosis, or kidney fibrosis), chronic and acute diseases of the liver (such as fatty liver disease, or liver steatosis), chronic and acute diseases of the lung, chronic and acute diseases of the kidney, myocardial infarction, cardiovascular disease, arrhythmias, atherosclerosis, spinal cord injury, ischemic stroke, and neuropathic pain.

Yet another aspect of the present invention is a pharmaceutical composition comprising at least one compound or a pharmaceutically acceptable salt, solvate, hydrate, tautomer or stereoisomer thereof of the present invention together with a pharmaceutically acceptable carrier, optionally in combination with one or more other bioactive compounds or pharmaceutical compositions.

Preferably, the one or more bioactive compounds are modulators of the integrated stress response pathway other than compounds of formula (I).

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like a mixture of compounds of formula (I) in the composition or other modulators of the integrated stress response pathway.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Starting materials for the synthesis of preferred embodiments of the invention may be purchased from commercially available sources such as Array, Sigma Aldrich, Acros, Fisher, Fluka, ABCR or can be synthesized using known methods by one skilled in the art.

In general, several methods are applicable to prepare compounds of the present invention. In some cases various strategies can be combined. Sequential or convergent routes may be used. Exemplary synthetic routes are described below.

EXAMPLES

I Chemical Synthesis

Experimental Procedures

The following Abbreviations and Acronyms are used:

aq aqueous
ACN acetonitrile
AcOH acetic acid
Brine saturated solution of NaCl in water
$BnONH_2 \cdot HCl$ O-benzylhydroxylamine hydrochloride
Boc tert-butoxycarbonyl
$Boc_2O$ di-tert-butyl dicarbonate
$CDCl_3$ deuterated chloroform
CV column volume
DCM dichloromethane
DCE 1,2-dichloroethane
DIAD diisopropyl azodicarboxylate
DMSO dimethyl sulfoxide
DMSO-$d_6$ deuterated dimethylsulfoxide
DIPEA N,N-diisopropylethylamine
DMF dimethyl formamide
DMAP N,N-dimethylpyridin-4-amine
$ESI^+$ positive ionisation mode
$ESI^-$ negative ionisation mode
EtOAc ethyl acetate
EtOH ethanol
$Et_2O$ diethyl ether
FCC flash column chromatography
$H_2O$ water
$H_2SO_4$ sulfuric acid
HATU 1-[bis(dimethylamino)methylidene]-1H-[1,2,3]triazolo[4,5-b]pyridin-1-ium 3-oxide hexafluorophosphate
HCl hydrochloric acid
HPLC high-performance liquid chromatography
h hour(s)
$KHCO_3$ potassium bicarbonate
$LiOH \cdot H_2O$ lithium hydroxide hydrate
LiHMDS lithium bis(trimethylsilyl)amide
m multiplet
MeOH methanol
MeMgBr methyl magnesium bromide
$MgSO_4$ magnesium sulphate
MHz megahertz
min minutes
MsOH methanesulfonic acid
mL millilitre (s)
$N_2$ nitrogen atmosphere
$Na_2SO_4$ sodium sulphate
$NaHCO_3$ sodium bicarbonate
NBS N-bromosuccinimide
$NH_4Cl$ ammonium chloride
NMR Nuclear Magnetic Resonance
$PPh_3$ triphenylphosphine prep. preparative
r.t. room temperature
RT retention time
satd saturated
TBME 2-methoxy-2-methylpropane
THF tetrahydrofuran
TMSOI trimethylsulfoxonium iodide
TMSCI chlorotrimethylsilane
$ZnBr_2$ zinc dibromide Analytical LCMS Conditions are as Follows System 1 (S1): Acidic IPC Method (MS18 and MS19)

Analytical (MET/CR/1410) HPLC-MS were performed on a Shimadzu LCMS systems using a Kinetex Core shell C18 column (2.1 mm×50 mm, 5 μm; temperature: 40° C.) and a gradient of 5-100% B (A=0.1% formic acid in $H_2O$; B=0.1% formic acid in ACN) over 1.2 min then 100% B for 0.1 min. A second gradient of 100-5% B was then applied over 0.01 min with an injection volume of 3 μL at a flow rate of 1.2 mL/min. UV spectra were recorded at 215 nm using a SPD-M20A photo diode array detector spectrum range: 200-400 nm. Mass spectra were obtained using a 2010EV detector. Data were integrated and reported using Shimadzu LCMS-Solutions and PsiPort software.

System 2 (S2): Acidic IPC Method (MSQ1, MSQ2, MSQ4 and MSQ6)

Analytical (MET/uPLC/1704) uHPLC-MS were performed on a Waters Acquity uPLC system using a Waters UPLC® BEH™ C18 column (2.1 mm×50 mm, 1.7 μm; temperature 40° C.) and a gradient of 5-100% B (A=0.1% formic acid in $H_2O$; B=0.1% formic acid in ACN) over 1.1 min then 100% B for 0.25 min. A second gradient of 100-5% B was then applied over 0.05 min and held for 0.1 min with an injection volume of 1 μL at a flow rate of 0.9 mL/min. UV spectra were recorded at 215 nm on a Waters Acquity PDA with a spectrum range of 200-400 nm. Mass spectra were obtained using a Waters QDa. Data were integrated and reported using Waters MassLynx and OpenLynx software.

System 3 (S3): Basic IPC Method (MS16)

Analytical (MET/CR/1602) uHPLC-MS were performed on a Waters Acquity uPLC system using Waters UPLC® BEH™ C18 column (2.1 mm×30 mm, 1.7 μm; temperature 40° C.) and a gradient of 5-100% B (A: 2 mM ammonium bicarbonate, buffered to pH 10, B: ACN) over min, then 100% B for 0.1 min. A second gradient of 100-5% B was then applied over 0.05 min and held for 0.1 min with an injection volume of 1 μL at a flow rate of 1 mL/min. UV spectra were recorded at 215 nm on a Waters Acquity PDA with a spectrum range of 200-400 nm. Mass spectra were obtained using a Waters Quattro Premier XE. Data were integrated and reported using Waters MassLynx and OpenLynx software.

System 4 (S4): Acidoc Final Method (MSQ1 and MSQ2)

Analytical (MET/uPLC/AB101) uHPLC-MS were performed on a Waters Acquity uPLC system using a Phenomenex Kinetex-XB C18 column (2.1 mm×100 mm, 1.7 μM; temperature: 40° C.) and a gradient of 5-100% B (A=0.1% formic acid in $H_2O$; B=0.1% formic acid in ACN) over 5.3 min then 100% B for 0.5 min. A second gradient of 100-5% B was then applied over 0.02 min and held for 1.18 min with an injection volume of 1 μL at flow rate of 0.6 mL/min. UV spectra were recorded at 215 nm using a Waters Acquity PDA detector spectrum range: 200-400 nm. Mass spectra were obtained using a Waters SQD (MSQ1) or Waters Acquity QDA (MSQ2). Data were integrated and reported using Waters MassLynx and OpenLynx software.

System 5 (S5): Acidic Final Method (MS18, MS19)

Analytical (MET/CR/1416) HPLC-MS were performed on Shimadzu LCMS systems using a Waters Atlantis dC18 column (2.1 mm×100 mm, 3 μm; temperature: 40° C.) and a gradient of 5-100% B (A=0.1% formic acid in $H_2O$; B=0.1% formic acid in ACN) over 5 min then 100% B for 0.4 min. A second gradient of 100-5% B was then applied over 0.02 min and held for 1.58 min with an injection volume of 3 μL at flow rate of 0.6 mL/min. UV spectra were recorded at 215 nm using a SPD-M20A photo diode array detector spectrum range: 200-400 nm. Mass spectra were obtained using a 2010EV detector. Data were integrated and reported using Shimadzu LCMS-Solutions and PsiPort software.

System 6 (S6): Basic Final Method (MS16)

Analytical (MET/uHPLC/AB105) uPLC-MS were performed on a Waters Acquity uPLC system using a Waters UPLC® BEH™ C18 column (2.1 mm×100 mm, 1.7 μm column; temperature: 40° C.) and a gradient of 5-100% (A=2 mM ammonium bicarbonate, buffered to pH 10; B=ACN) over 5.3 min then 100% B for 0.5 min. A second gradient of 100-5% B was then applied over 0.02 min and held for 1.18 min with an injection volume of 1 μL and at flow rate of 0.6 mL/min. UV spectra were recorded at 215 nm using a Waters Acquity photo diode array detector Spectrum range: 200-400 nm. Mass spectra were obtained using a Waters Quattro Premier XE mass detector. Data were integrated and reported using Waters MassLynx and OpenLynx software.

Purification Methods Are as Follows:

Method 1: Acidic Early Method

Purifications (P1) LC were performed on a Gilson LC system using a Waters Sunfire C18 column (30 mm×100 mm, 10 μM; temperature: r.t.) and a gradient of 10-95% B (A=0.1% formic acid in $H_2O$; B=0.1% formic acid in ACN) over 14.44 min then 95% B for 2.11 min. A second gradient of 95-10% B was then applied over 0.2 min with an injection volume of 1500 μL at flow rate of 40 mL/min. UV spectra were recorded at 215 nm using a Gilson detector.

Method 2: Acidic Standard Method

Purifications (P2) LC were performed on a Gilson LC system using a Waters Sunfire C18 column (30 mm×10 mm, 10 μM; temperature: r.t.) and a gradient of 30-95% B (A=0.1% formic acid in water; B=0.1% formic acid in ACN) over 11.00 min then 95% B for 2.10 min. A second gradient of 95-30% B was then applied over 0.2 min with an injection volume of 1500 μL at flow rate of 40 mL/min. UV spectra were recorded at 215 nm using a Gilson detector.

Method 3: Basic Early Method

Purifications (P3) LC were performed on a Gilson LC system using a Waters X-Bridge C18 column (30 mm×100 mm, 10 μM; temperature: r.t.) and a gradient of 10-95% B (A=0.2% $NH_4OH$ in $H_2O$; B=0.2% $NH_4OH$ in ACN) over 14.44 min then 95% B for 2.11 min. A second gradient of 95-10% B was then applied over 0.2 min with an injection volume of 1500 μL at flow rate of 40 mL/min. UV spectra were recorded at 215 nm using a Gilson detector.

Method 4: Basic Standard Method

Purifications (P4) LC were performed on a Gilson LC system using a Waters X-Bridge C18 column (30 mm×10 mm, 10 μM; temperature: r.t.) and a gradient of 30-95% B (A=0.2% $NH_4OH$ in water; B=0.2% $NH_4OH$ in ACN) over 11.00 min then 95% B for 2.10 min. A second gradient of 95-30% B was then applied over 0.21 min with an injection volume of 1500 μL at flow rate of 40 mL/min. UV spectra were recorded at 215 nm using a Gilson detector.

Method 5: Reverse Phase Chromatography Using Acidic pH, Standard Elution Method

Purifications by FCC on reverse phase silica (acidic pH, standard elution method) were performed on Biotage Isolera systems using the appropriate SNAP C18 cartridge and a gradient of 10% B (A=0.1% formic acid in $H_2O$; B=0.1% formic acid in ACN) over 1.7 CV then 10-100% B over 19.5 CV and 100% B for 2 CV.

Method 6: Reverse Phase Chromatography Using Basic pH, Standard Elution Method

Purifications by FCC on reverse phase silica (basic pH, standard elution method) were performed on Biotage Isolera systems using the appropriate SNAP C18 cartridge and a gradient of 10% B (A=0.1% $NH_3$ in $H_2O$; B=0.1% $NH_3$ in ACN) over 1.7 CV then 10-100% B over 19.5 CV and 100% B for 2 CV.

NMR Conditions

Unless otherwise stated, $^1H$ NMR spectra were recorded at 500 MHz, 400 MHz or 250 MHz on either a Bruker Avance III HD 500 MHz spectrometer, Bruker Avance III HD 400 MHz spectrometer or Bruker Avance III HD 250 MHz spectrometer respectively. Chemical shifts, δ, are quoted in parts per million (ppm) and are referenced to the residual solvent peak. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

General Synthesis

All the compounds have been synthesised with a purity >95% unless otherwise specified.

Scheme for route 1

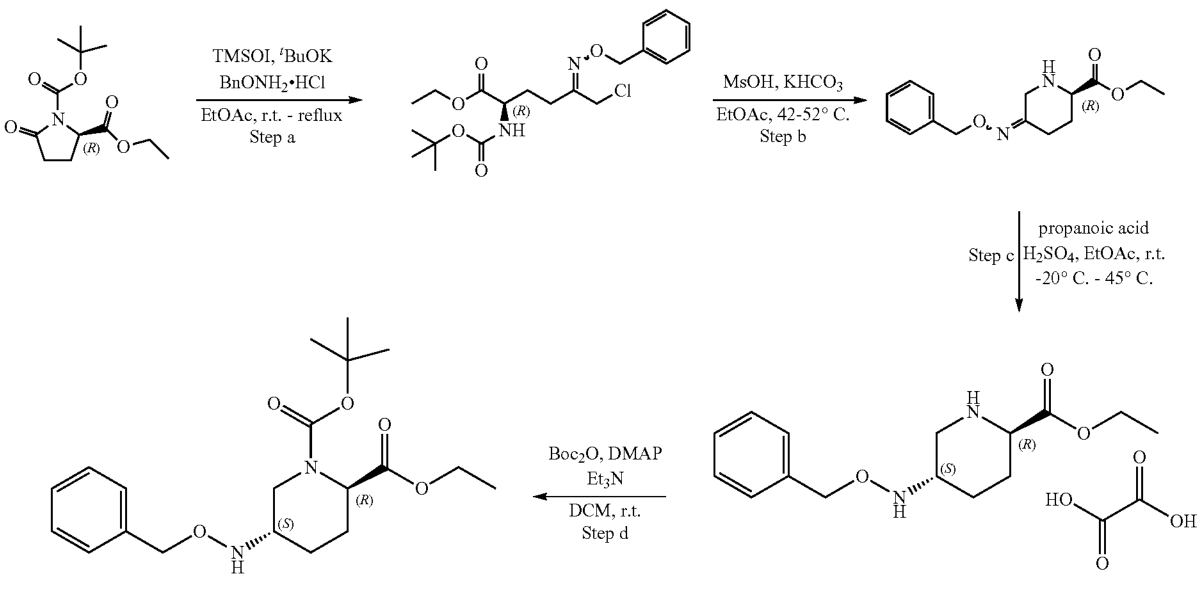

Intermediate 1

Step 1.a: ethyl (2R)-5-[(benzyloxy)imino]-2-{[(tert-butoxy)carbonyl]amino}-6-chlorohexanoate

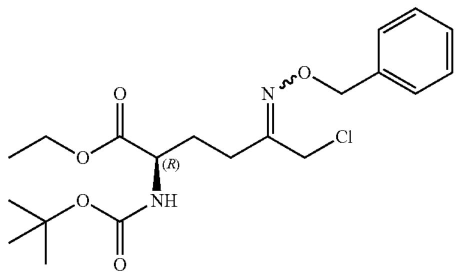

DMSO (75 mL) was added to a solution of TMSOI (12.89 g, 58.3 mmol) and ᵗBuOK (6.27 g, 55.9 mmol) in THF (anhydrous, 60 mL) and the mixture was stirred at r.t. for 1 h. The reaction mixture was cooled to −12° C. and a solution of ethyl Boc-D-Pyroglutamate (12.5 g, 48.6 mmol) in THF (anhydrous, 38 mL) was added and stirred at r.t. for 16 h. The reaction mixture was diluted with satd aq $NH_4Cl$ solution (80 mL), $H_2O$ (15 mL) and EtOAc (200 mL), and the organic layer was isolated, washed with brine, and concentrated in vacuo to approximately 100 mL. A solution of $BnONH_2 \cdot HCl$ (8.14 g, 51.0 mmol) in EtOAc (62 mL), was added and the mixture was stirred at reflux for 2 h. The reaction mixture was cooled to r.t., washed with $H_2O$ and brine, and the organic layer was concentrated in vacuo to afford the title compound (85% purity, 19.5 g, 40.1 mmol, 83% yield) as a colourless oil; $^1H$ NMR (400 MHz, chloroform-d) δ 7.16-7.33 (m, 5H), 5.01-5.06 (m, 2H), 3.95-4.30 (m, 5H), 2.32-2.50 (m, 2H), 1.98-2.13 (m, 1H), 1.75-1.92 (m, 1H), 1.30-1.40 (m, 9H), 1.12-1.24 (m, 3H), Step 1.b: ethyl (2R)-5-[(benzyloxy)imino]piperidine-2-carboxylate

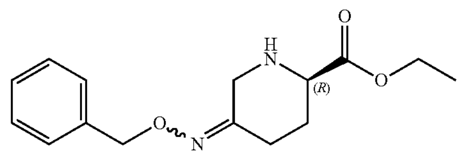

To a solution of ethyl (2R)-5-[(benzyloxy)imino]-2-{[(tert-butoxy)carbonyl]amino}-6-chlorohexanoate (85% purity, 19.5 g, 40.1 mmol) in EtOAc (157 mL) was added MsOH (7.8 mL, 0.12 mol) and the mixture was stirred at 42° C. for 2 h. The resultant mixture was added to a solution of $KHCO_3$ (20.1 g, 0.201 mol) in $H_2O$ (100 mL) and stirred at 52° C. for 2 h. The reaction mixture was cooled to r.t. and the organic layer was isolated, washed with brine, dried over $Na_2SO_4$, and concentrated in vacuo to afford the title compound (85% purity, 13.0 g, 40.0 mmol) in quantitative yield as a dark orange oil; $^1H$ NMR (400 MHz, chloroform-d) δ 7.20-7.34 (m, 5H), 4.99 (d, J=4.8 Hz, 2H), 4.13 (q, J=7.1 Hz, 2H), 3.45-3.56 (m, 1H), 3.25 (dd, J=14.9, 9.8 Hz, 1H), 3.08 (dt, J=14.5, 4.3 Hz, 1H), 2.01-2.32 (m, 3H), 1.55-1.80 (m, 1H), 1.21 (t, J=7.1 Hz, 3H).

Step 1.c: ethyl (2R,5S)-5-[(benzyloxy)amino]piperidine-2-carboxylate oxalic acid

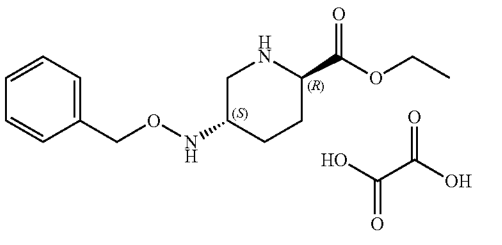

Propanoic acid (23 mL, 0.240 mol) was added to a suspension of $NaBH_4$ (3.03 g, 80.0 mmol) in EtOAc (95 mL) and the mixture was stirred at r.t. for 1 h. The resultant mixture was added to a solution of ethyl (2R)-5-[(benzyloxy)imino]piperidine-2-carboxylate (85% purity, 13.0 g, mmol) in EtOAc (95 mL) and $H_2SO_4$ (11 mL, 0.20 mol) at −20° C. and stirred at r.t. for 60 h. The reaction mixture was diluted with $H_2O$ (75 mL) and neutralised with aq $NH_4OH$ solution. The organic layer was isolated, washed with brine, dried over $Na_2SO_4$, and concentrated in vacuo to ~75 mL volume. The solution was warmed to 45° C., and MeOH (30 mL), followed by a solution of oxalic acid (3.60 g, 40.0 mmol) in MeOH (15 mL) was added. The mixture was cooled to 0° C., and the resultant precipitate was isolated via vacuum filtration, washing with MeOH:EtOH (1:4) and EtOAc to afford the title compound (7.17 g, 19.1 mmol, 48% yield); $^1H$ NMR (500 MHz, DMSO-$d_6$) δ 7.25-7.42 (m, 5H), 4.59 (s, 2H), 4.17-4.24 (m, 2H), 3.92 (dd, J=12.3, 3.2 Hz, 1H), 3.34-3.40 (m, 1H), 3.10 (ddd, J=15.1, 7.6, 3.9 Hz, 1H), 2.64 (t, J=11.5 Hz, 1H), 2.13 (dt, J=10.2, 3.4 Hz, 1H), 1.87 (dd, J=9.0, 3.8 Hz, 1H), 1.65 (qd, J=13.2, 3.6 Hz, 1H), 1.40 (qd, J=12.8, 3.9 Hz, 1H), 1.23 (t, J=7.1 Hz, 3H); M/Z: 279, $[M+H]^+$, $ESI^+$, RT=0.81 (S1).

Intermediate 1 (Step 1.d): 1-tert-butyl 2-ethyl (2R,5S)-5-[(benzyloxy)amino]piperidine-1,2-dicarboxylate Intermediate 1

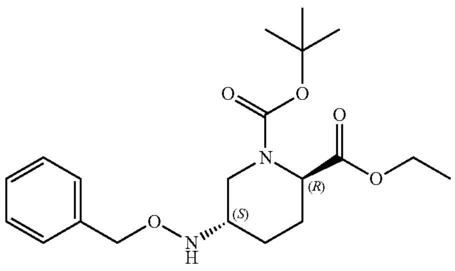

To a solution of ethyl (2R,5S)-5-[(benzyloxy)amino]piperidine-2-carboxylate oxalic acid (2.22 g, 6.03 mmol) in DCM (anhydrous, 30 mL) at 0° C. was added $Et_3N$ (3.6 mL, 25.8 mmol), DMAP (76 mg, 0.622 mmol) and $Boc_2O$ (4.2 mL, 18.3 mmol) and the mixture was stirred at r.t. for 17 h. The reaction mixture was diluted with satd aq $NH_4Cl$ solution and DCM, and the organic layer was isolated, washed with $H_2O$ and brine, dried over $Na_2SO_4$, and concentrated in vacuo. Purification by FCC on silica gel (0-20% EtOAc in heptane) afforded the title compound (86% purity, 1.40 g, 3.18 mmol, 53% yield) as a colourless oil; $^1H$ NMR (500 MHz, chloroform-d) δ 7.40-7.26 (m, 5H), 5.51-5.41 (m, 1H), 4.92-4.80 (m, 1H), 4.79-4.62 (m, 2H), 4.19 (q, J=7.0 Hz, 3H), 3.11 (d, J=45.4 Hz, 2H), 1.96 (s, 2H), 1.73-1.60 (m, 1H), 1.55-1.49 (m, 1H), 1.46 (s, 9H), 1.27 (t, J=7.1 Hz, 3H); M/Z: 379, $[M+H]^+$, $ESI^+$, RT=1.09 (S2).

Scheme for route 2

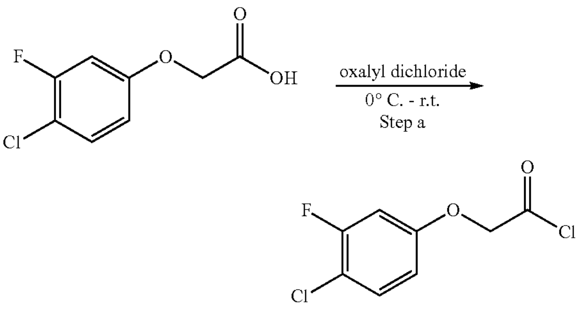

Intermediate 2

Intermediate 2 (Step 2.a): 2-(4-chloro-3-fluorophenoxy)acetyl chloride

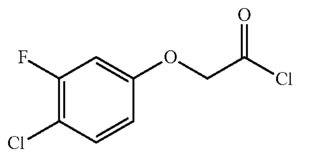

Intermediate 2

To a solution of 2-(4-chloro-3-fluorophenoxy)acetic acid (5.16 g, 22.7 mmol) in DCM (45 mL) at 0° C. was added oxalyl dichloride (10 mL, 0.115 mol) followed by DMF (81 μL, 1.11 mmol) and the mixture was stirred at r.t. for 17 h. The reaction mixture was concentrated in vacuo to afford the title compound (90% purity, 5.30 g, 21.4 mmol, 94% yield) as an orange oil; $^1$H NMR (400 MHz, chloroform-d) δ 7.31 (t, J=8.6 Hz, 1H), 6.75 (dt, J=10.2, 2.9 Hz, 1H), 6.66 (ddd, J=8.9, 2.9, 1.2 Hz, 1H), 4.96 (s, 2H).

Scheme for route 3

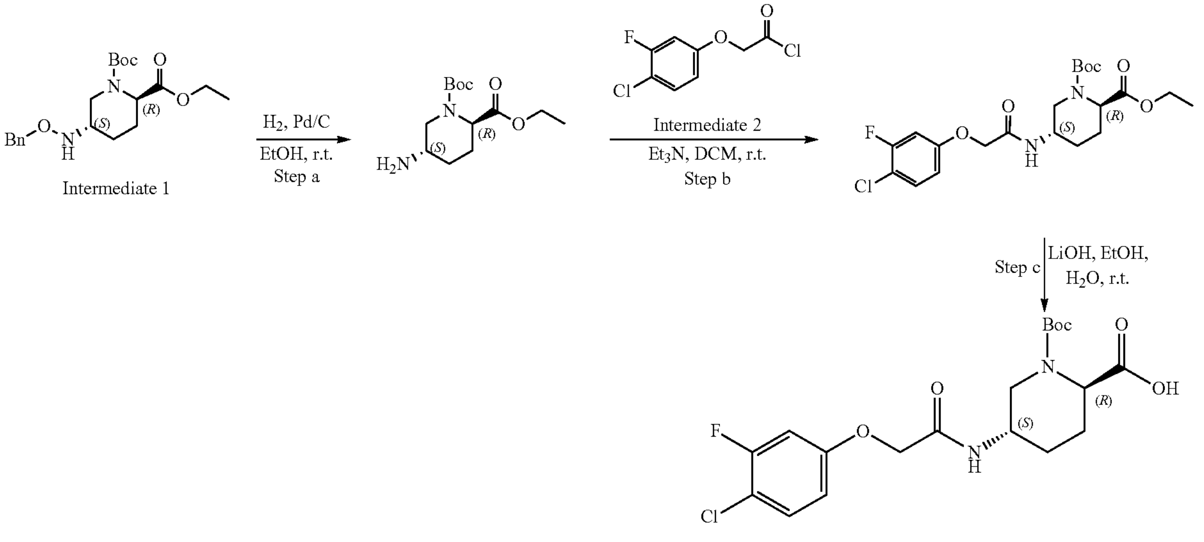

Step 3.a: 1-tert-butyl 2-ethyl (2R,5S)-5-aminopiperidine-1,2-dicarboxylate

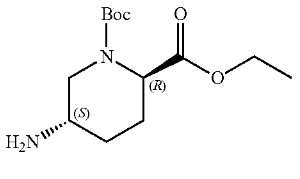

To a solution of 1-tert-butyl 2-ethyl (2R,5S)-5-[(benzyloxy)amino]piperidine-1,2-dicarboxylate (93% purity, 8.7 g, 21.3 mmol, Intermediate 1) in EtOH (anhydrous, 200 mL) under $N_2$ was added Pd/C (10%, 2.28 g, 2.14 mmol) and the mixture was stirred under $H_2$ at r.t. for 17 h. The reaction mixture was filtered through a pad of Celite and the filtrate concentrated in vacuo. The residue was purified using an SCX-2 cartridge, first flushing with MeOH and second eluting with 3 M $NH_3$ in MeOH to afford the title compound (4.88 g, 17.0 mmol, 80% yield) as a pale yellow oil; $^1$H NMR (400 MHz, chloroform-d) δ 4.98-4.57 (m, 1H), 4.18 (q, J=7.1 Hz, 2H), 3.87-3.64 (m, 1H), 3.35-2.99 (m, 2H), 2.14-1.92 (m, 2H), 1.64-1.52 (m, 2H), 1.45 (s, 11H), 1.26 (t, J=7.1 Hz, 3H).

Step 3.b: 1-tert-butyl 2-ethyl (2R,5S)-5-[2-(4-chloro-3-fluorophenoxy)acetamido] piperidine-1,2-dicarboxylate

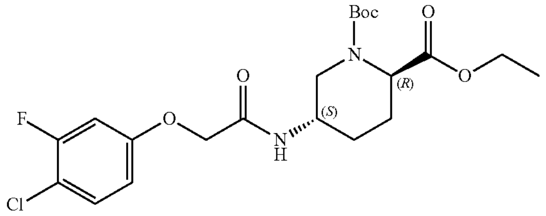

To a mixture of 1-tert-butyl 2-ethyl (2R,5S)-5-aminopiperidine-1,2-dicarboxylate (4.88 g, 17.0 mmol) and $Et_3N$ (14 mL, 0.103 mol) in DCM (170 mL) at 0° C. was added dropwise a solution of 2-(4-chloro-3-fluoro-phenoxy)acetyl chloride (4.19 g, 18.8 mmol, Intermediate 2) in DCM (10 mL) and stirred at r.t. for 48 h. The reaction mixture was diluted with DCM (250 mL) and washed with satd aq $NaHCO_3$ solution (2×100 mL) and brine (100 mL), dried over $Na_2SO_4$ and concentrated in vacuo. Purification by FCC on silica gel (0-50% EtOAc in heptane) afforded the title compound (7.14 g, 15.6 mmol, 91% yield) as a colourless oil; $^1$H NMR (400 MHz, chloroform-d) δ 7.32 (t, J=8.6 Hz, 1H), 6.86-6.72 (m, 2H), 6.69-6.63 (m, 1H), 4.98-4.66 (m, 1H), 4.45 (s, 2H), 4.29-4.13 (m, 3H), 4.09-3.87 (m, 1H), 3.33-3.10 (m, 1H), 2.23-2.02 (m, 1H), 2.00-1.71 (m, 2H), 1.56 (s, 1H), 1.44 (s, 9H), 1.28 (t, J=7.2 Hz, 3H); M/Z: 459, 461 $[M+H]^+$, $ESI^+$, RT=3.83 (S4).

Intermediate 3 (Step 3.c): (2R,5S)-1-[(tert-butoxy) carbonyl]-5-[2-(4-chloro-3-fluorophenoxy)acetamido]piperidine-2-carboxylic acid Intermediate 3

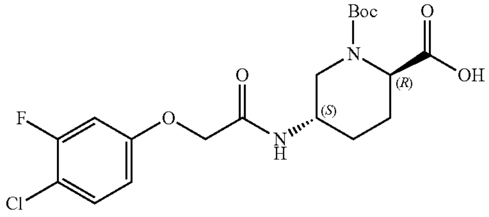

LiOH (0.78 g, 31.1 mmol) was added to a solution of 1-tert-butyl 2-ethyl (2R,55)-5-[2-(4-chloro-3-fluorophenoxy)acetamido] piperidine-1,2-dicarboxylate (7.1 g, 15.6 mmol) in EtOH (80 mL) and $H_2O$ (20 mL) and the mixture was stirred at r.t. for 3 h. The reaction mixture was concentrated in vacuo, dissolved in $H_2O$ (50 mL), and extracted with DCM (2×100 mL). The aqueous layer was then acidified to pH 2 using 2 M aq HCl solution and extracted with EtOAc (3×100 mL). The combined organic extracts were washed with brine (100 mL), dried over anhydrous $Na_2SO_4$, and concentrated in vacuo to afford the title compound (87% purity, 5.60 g, 11.3 mmol, 73% yield) as a white solid; $^1$H NMR (400 MHz, DMSO-$d_6$) δ 8.02 (d, J=7.3 Hz, 1H), 7.47 (t, J=8.9 Hz, 1H), 7.03 (dd, J=11.4, 2.8 Hz, 1H), 6.83-6.75 (m, 1H), 4.59-4.54 (m, 2H), 3.93 (s, 1H), 3.73 (d, J=54.2 Hz, 1H), 3.13-2.94 (m, 1H), 2.06-1.87 (m, 2H), 1.61 (d, J=12.2 Hz, 1H), 1.56-1.43 (m, 1H), 1.37 (s, 10H); M/Z: 429, 431 [M+H], $ESI^+$, RT=0.91 min (S1).

Scheme for route 4

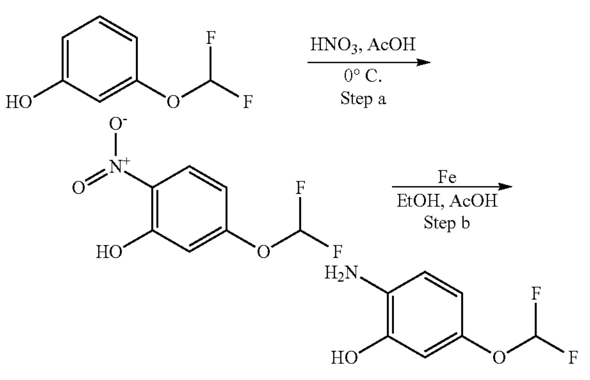

Intermediate 4

Step 4.a: 5-(difluoromethoxy)-2-nitrophenol

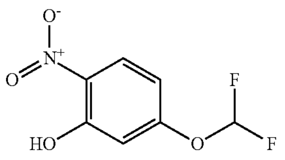 [SMILES: O=[N+]([O-])c1ccc(OC(F)F)cc1O]

To a solution of the 3-(difluoromethoxy)phenol (1.50 g, 9.37 mmol) in acetic acid (8.0 mL, 9.37 mmol) at 0° C. was slowly added nitric acid (0.43 mL, 10.3 mmol). The reaction mixture was stirred for 10 min, then diluted with $H_2O$ (50 mL) and extracted with EtOAc (3×50 mL). The combined organic extracts were dried over $MgSO_4$, concentrated in vacuo and purified by FCC on silica gel (0-100% EtOAc in heptane) to afford the title compound (90% purity, 780 mg, 3.42 mmol, 37% yield) as a brown gum; $^1$H NMR (500 MHz, DMSO-$d_6$) δ 11.31 (s, 1H), 8.04 (d, J=9.1 Hz, 1H), 7.31 (t, J=72.9 Hz, 1H), 6.82 (dd, J=9.1, 2.5 Hz, 1H), 6.77 (d, J=2.4 Hz, 1H).

Intermediate 4 (Step 4.b): 2-amino-5-(difluoromethoxy)phenol

Intermediate 4

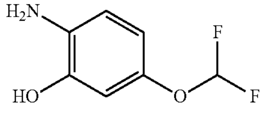

To a solution of the 5-(difluoromethoxy)-2-nitrophenol (90% purity, 780 mg, 3.42 mmol) in EtOH (14 mL) was added AcOH (7 mL) and iron (1.91 g, 34.2 mmol) and the mixture was stirred at 100° C. for 1 h. The reaction mixture was diluted with $H_2O$ (25 mL) and basified to pH 8 using 1 M aq NaOH solution. The resultant solution was extracted with EtOAc (50 mL) and the combined organic extracts were washed with $H_2O$ (25 mL) and brine (25 mL), dried over $MgSO_4$, and concentrated in vacuo to afford the title compound (50% purity, 800 mg, 2.28 mmol, 67% yield) as a black oil; $^1$H NMR (400 MHz, DMSO-$d_6$) δ 8.76 (s, 1H), 6.97 (t, J=74.8 Hz, 1H), 6.62 (d, J=8.4 Hz, 1H), 6.48-6.42 (m, 2H), 4.34 (s, 2H).

Scheme for route 5

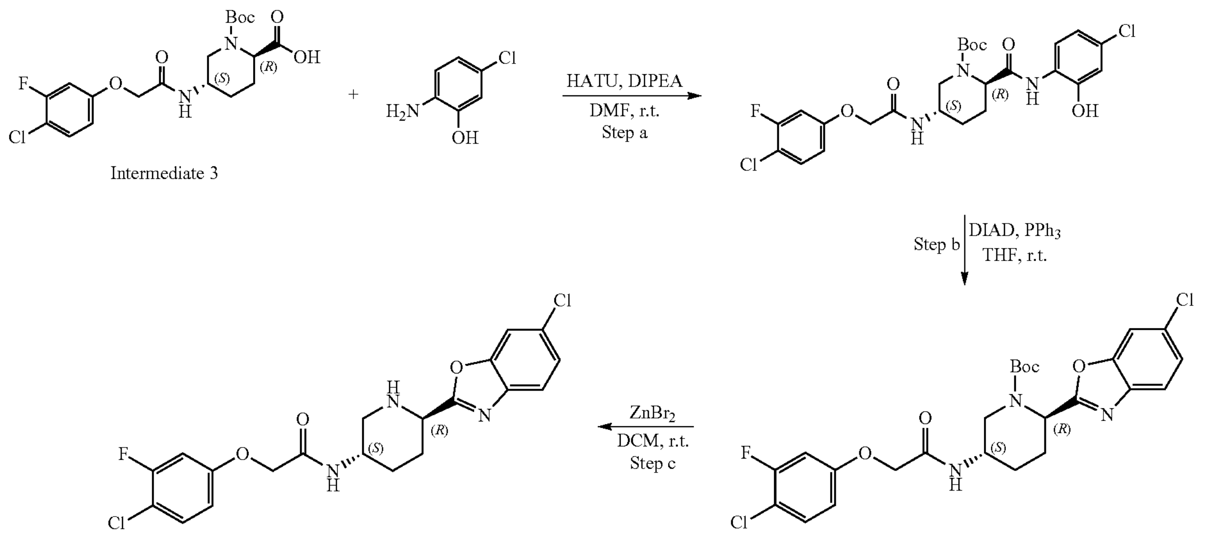

Example 2

Example 1

Step 5.a: tert-butyl (2R,5S)-2-[(4-chloro-2-hydroxyphenyl)carbamoyl]-5-[2-(4-chloro-3-fluorophenoxy)acetamido]piperidine-1-carboxylate

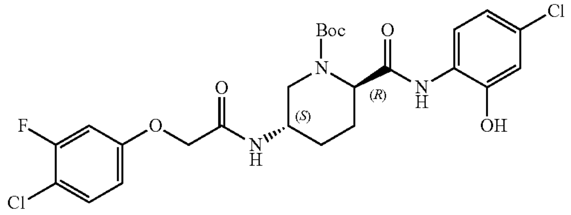

To a solution of 2-amino-5-chlorophenol (167 mg, 1.16 mmol), DIPEA (0.61 mL, 3.48 mmol) and (2R,5S)-1-[(tert-butoxy)carbonyl]-5-[2-(4-chloro-3-fluorophenoxy)acetamido]piperidine-2-carboxylic acid (500 mg, 1.16 mmol, Intermediate 3) in DMF (anhydrous, 16 mL) was added HATU (441 mg, 1.16 mmol) and the mixture was stirred at r.t. for 3 h. The reaction mixture was diluted with EtOAc (30 mL), washed with water (2×20 mL), and the combined organic extracts were dried over $MgSO_4$ and concentrated in vacuo. Purification by FCC on silica gel (10-100% EtOAc in heptane) afforded the title compound (90% purity, 256 mg, 0.414 mmol, 36% yield) as a brown oil; $^1H$ NMR (400 MHz, $CDCl_3$) δ 8.45 (s, 1H), 7.37-7.30 (m, 1H), 7.14-7.04 (m, 1H), 7.01-6.98 (m, 1H), 6.87-6.65 (m, 3H), 4.93 (s, 1H), 4.53-4.41 (m, 2H), 4.30-4.13 (m, 2H), 3.21-3.10 (m, 1H), 2.41-2.13 (m, 1H), 1.97-1.57 (m, 5H), 1.52-1.40 (m, 9H); M/Z: 556, 558 $[M+H]^+$, $ESI^+$, RT=4.24 min (S4).

Example 1 (Step 5.b): tert-butyl (2R,5S)-2-(6-chloro-1,3-benzoxazol-2-yl)-5-[2-(4-chloro-3-fluorophenoxy)acetamido]piperidine-1-carboxylate Example 1

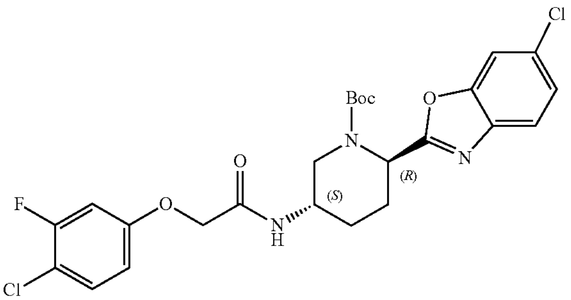

To a solution of tert-butyl (2R,5S)-2-[(4-chloro-2-hydroxyphenyl)carbamoyl]-5-[2-(4-chloro-3-fluorophenoxy)acetamido]piperidine-1-carboxylate (90% purity, 200 mg, 0.324 mmol) and DIAD (76 μL, 0.388 mmol) in THF (anhydrous, 4 mL) at 0° C. was added $PPh_3$ (110 mg, 0.421 mmol) and the mixture was stirred at r.t. for 1 h. The reaction mixture was diluted with EtOAc (10 mL), washed with $H_2O$ (2×10 mL), and the organic extracts were dried over $MgSO_4$ and concentrated in vacuo. Purification by FCC on silica gel (0-100% EtOAc in heptane) afforded the title compound (90% purity, 170 mg, 0.284 mmol, 88% yield) as a colourless oil; $^1H$ NMR (500 MHz, $CDCl_3$) δ 7.64-7.59 (m, 1H), 7.55-7.51 (m, 1H), 7.37-7.31 (m, 2H), 6.96-6.80 (m, 1H), 6.80-6.75 (m, 1H), 6.72-6.66 (m, 1H), 4.54-4.43 (m, 2H), 4.20-4.15 (m, 1H), 2.34 (s, 1H), 2.07-1.75 (m, 6H), 1.47 (s, 9H); M/Z: 438, 440 $[M-Boc+H]^+$, $ESI^+$, RT=1.16 min (S2).

Example 2 (Step 5.c): N-[(3S,6R)-6-(6-chloro-1,3-benzoxazol-2-yl)piperidin-3-yl]-2-(4-chloro-3-fluorophenoxy)acetamide Example 2

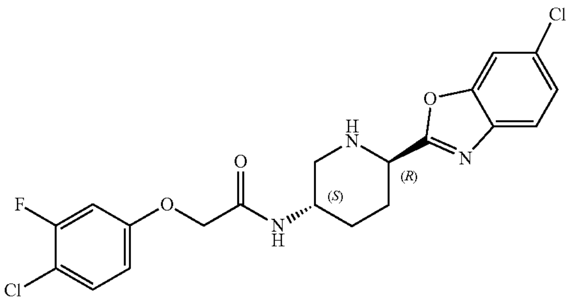

To a solution of tert-butyl (2R,5S)-2-(6-chloro-1,3-benzoxazol-2-yl)-5-[2-(4-chloro-3-fluorophenoxy)acetamido] piperidine-1-carboxylate (90% purity, 80 mg, 0.134 mmol, Example 1) in DCM (anhydrous, 2.5 mL) was added $ZnBr_2$ (90 mg, 0.401 mmol) and the mixture was stirred at r.t. for 16 h. The reaction mixture was diluted with EtOAc (15 mL), washed with $H_2O$ (2×8 mL), and the organic extracts were dried over $MgSO_4$ and concentrated in vacuo. Purification by prep. HPLC (Method 3) afforded the title compound (8.2 mg, 0.0187 mmol, 14% yield) as a white solid; $^1H$ NMR (400 MHz, DMSO-$d_6$) δ 7.99 (d, J=8.1 Hz, 1H), 7.91 (d, J=1.9 Hz, 1H), 7.74 (d, J=8.5 Hz, 1H), 7.50 (t, J=8.9 Hz, 1H), 7.42 (dd, J=8.5, 2.0 Hz, 1H), 7.07 (dd, J=11.4, 2.8 Hz, 1H), 6.86 (ddd, J=9.0, 2.8, 1.1 Hz, 1H), 4.53 (s, 2H), 3.98-3.90 (m, 1H), 3.78-3.69 (m, 1H), 3.09-3.00 (m, 1H), 2.93-2.84 (m, 1H), 2.16-2.06 (m, 1H), 1.99-1.89 (m, 1H), 1.81-1.69 (m, 1H), 1.62-1.49 (m, 1H); M/Z: 438, 440 $[M+H]^+$, $ESI^+$, RT=2.27 min (S4).

The example compounds in Table 1 were synthesised according to general route 5 as exemplified by Examples 1 and 2 using the corresponding intermediates.

TABLE 1

| Ex | Structure | Name | Intermediates | LCMS data | $^1H$ NMR |
|---|---|---|---|---|---|
| 3 | 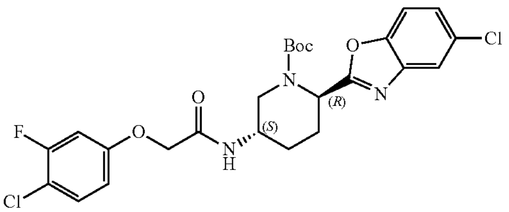 | tert-butyl (2R,5S)-2-(5-chloro-1,3-benzoxazol-2-yl)-5-[2-(4-chloro-3-fluoro-phenoxy) acetamido] piperidine-1-carboxylate | (2R,5S)-1-[(tert-butoxy) carbonyl 1-5-[2-(4-chloro-3-fluoro-phenoxy) acetamido] piperidine-2-carboxylic acid (Intermediate 3) and 2-amino-4-chlorophenol | M/Z: 438, 440 [M − Boc + $H]^+$, $ESI^+$, RT = 1.15, 95% purity (S2) | |
| 4 | 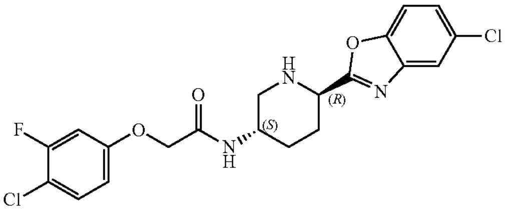 | N-[(3S,6R)-6-(5-chloro-1,3-benzoxazol-2-yl) piperidin-3-yl]-2-(4-chloro-3-fluoro-phenoxy) acetamide | (2R,5S)-1-[(tert-butoxy) carbonyl]-5-[2-(4-chloro-3-fluoro-phenoxy) acetamido] piperidine-2-carboxylic acid (Intermediate 3)and 2-amino-4-chlorophenol | M/Z: 438, 440 [M + $H]^+$, $ESI^+$, RT = 2.16 (S4). | $^1H$ NMR (400 MHz, DMSO-$d_6$) δ 7.99 (d, J = 8.1 Hz, 1H), 7.85 (d, J = 1.9 Hz, 1H), 7.76 (d, J = 8.7 Hz, 1H), 7.51 (t, J = 8.9 Hz, 1H), 7.44 (dd, J = 8.7, 2.1 Hz, 1H), 7.09 (dd, J= 11.4, 2.8 Hz, 1H), 6.87 (ddd, J = 9.0, 2.8, 1.1 Hz, 1H), 4.54 (s, 2H), 4.01-3.91 (m, 1H), 3.82-3.70 (m, 1H), 3.11-3.01 (m, 1H), 2.96-2.87 (m, 1H), 2.18-2.08 (m, 1H), 2.01-1.90 (m,1H), 1.83-1.71 (m, 1H), 1.63-1.49 (m, 1H). |

TABLE 1-continued

| Ex | Structure | Name | Intermediates | LCMS data | $^1$H NMR |
|---|---|---|---|---|---|
| 9 | 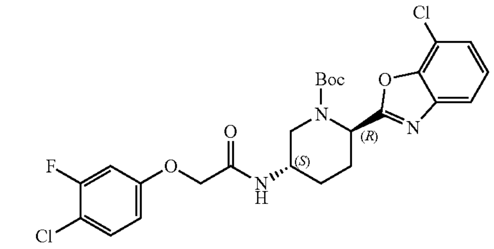 | tert-butyl (2R,5S)-2-(7-chloro-1,3-benzoxazol-2-yl)-5-[2-(4-chloro-3-fluoro-phenoxy) acetamido] piperidine-1-carboxylate | (2R,5S)-1-[(tert-butoxy) carbonyl]-5-[2-(4-chloro-3-fluorophenoxy) acetamido] piperidine-2-carboxylic acid (Intermediate 3) and 2-amino-6-chlorophenol | M/Z: 438, 440 [M − Boc + H]$^+$, ESI$^+$, RT = 1.03, 76% purity (S2). | |
| 10 | 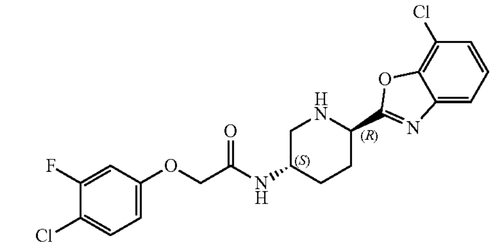 | N-[(3S,6R)-6-(7-chloro-1,3-benzoxazol-2-yl)piperidin-3-yl]-2-(4-chloro-3-fluoro-phenoxy) acetamide | (2R,5S)-1-[(tert-butoxy) carbonyl]-5-[2-(4-chloro-3-fluorophenoxy) acetamido] piperidine-2-carboxylic acid (Intermediate 3) and 2-amino-6-chlorophenol | M/Z: 438, 440 [M + H]$^+$, ESI$^+$, RT = 2.21 (S4). | $^1$H NMR (400 MHz, DMSO-$d_6$) δ 7.99 (d, J = 8.0 Hz, 1H), 7.72 (dd, J = 7.9, 0.8 Hz, 1H), 7.53-7.48 (m, 2H), 7.39 (t, J = 8.0 Hz, 1H), 7.08 (dd, J =11.4, 2.8 Hz, 1H), 6.86 (ddd, 1H), 4.54 (s, 2H), 4.02-3.96 (m, 1H), 3.81-3.70 (m, 1H), 3.06 (d, J = 12.3 Hz, 1H), 2.95-2.89 (m, 1H), 2.54 (d, J = 4.2 Hz, 1H), 2.17-2.10 (m, 1H), 2.00-1.92 (m, 1H), 1.84-1.72 (m, 1H), 1.63-1.50 (m,1H). |
| 11 | 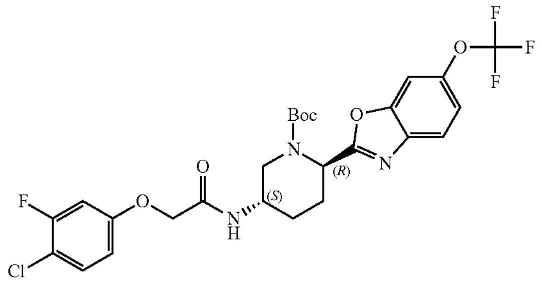 | tert-butyl (2R,5S)-5-[2-(4-chloro-3-fluoro-phenoxy) acetamido]-2-[6-(trifluoro-methoxy)-1,3-benzoxazol-2-yl] piperidine-1-carboxylate | (2R,5S)-1-[(tert-butoxy) carbonyl1-5-[2-(4-chloro-3-fluorophenoxy) acetamido] piperidine-2-carboxylic acid (Intermediate 3) and 2-amino-5-(trifluoro-methoxy) phenol hydrochloride | M/Z: 488, 490 [M − Boc + H]$^+$, ESI$^+$, RT = 1.18, 81% purity (S2) | |
| 12 | 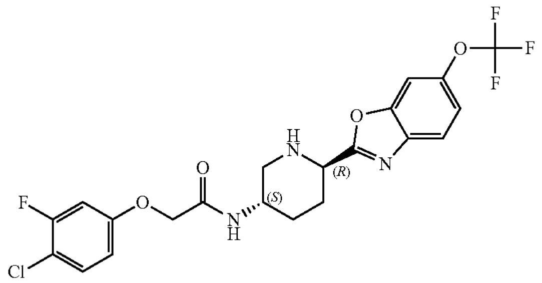 | 2-(4-chloro-3-fluoro-phenoxy)-N-[(3S,6R)-6-[6-(trifluoro-methoxy)-1,3-benzoxazol-2-yl]piperidin-3-yl]acetamide | (2R,5S)-1-[(tert-butoxy) carbonyl 1-5-[2-(4-chloro-3 fluorophenoxy) acetamido] piperidine-2-carboxylic acid (Intermediate 3) and 2-amino-5-(trifluoro-methoxy) phenol hydrochloride | M/Z: 488, 490 [M + H]$^+$, ESI$^+$, RT = 2.37 (S4). | $^1$H NMR (400 MHz, DMSO-$d_6$) δ 7.99 (d, J = 8.0 Hz, 1H), 7.93-7.89 (m, 1H), 7.85 (d, J = 8.7 Hz, 1H), 7.51 (t, J = 8.9 Hz, 1H), 7.40 (dd, J = 8.7, 1.3 Hz, 1H), 7.09 (dd, J = 11.4, 2.8 Hz, 1H), 6.87 (ddd, J = 9.0, 2.8, 1.1 Hz, 1H), 4.54 (s, 2H), 4.02-3.93 (m, 1H), 3.82-3.70 (m, 1H), 3.11-3.02 (m, 1H), 2.95-2.87 (m, 1H), 2.55-2.52 (m, 1H), 2.17-2.08 (m,1H), 1.98-1.91 (m, 1H), 1.83-1.72 (m, 1H), 1.63-1.50 (m, 1H). |

TABLE 1-continued

| Ex | Structure | Name | Intermediates | LCMS data | $^1$H NMR |
|---|---|---|---|---|---|
| 13 | 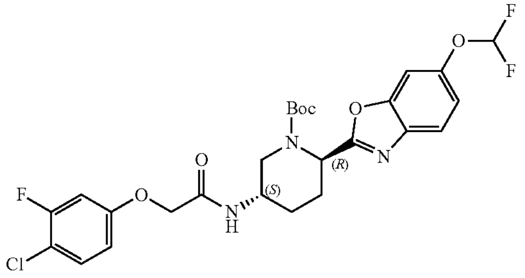 | tert-butyl (2R,5S)-5-[2-(4-chloro-3-fluoro-phenoxy) acetamido]-2-[6-(difluoro-methoxy)-1,3-benzoxazol-2-yl]piperidine-1-carboxylate | (2R,5S)-1-[(tert-butoxy) carbonyl 1-5-[2-(4-chloro-3-fluorophenoxy) acetamido] piperidine-2-carboxylic acid (Intermediate 3) nd 2-amino-5-(difluoro-methoxy) phenol (Intermediate 4) | M/Z: 470, 472 [M − Boc + H]$^+$, ESI$^+$, RT = 1.12, 30% purity (S2). | |
| 14 | 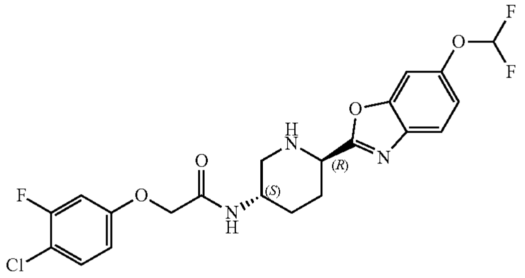 | 2-(4-chloro-3-fluoro-phenoxy)-N-[(3S,6R)-6-[6-(difluoro-methoxy)-1,3-benzoxazol-2-yl] piperidin-3-yl]acetamide | (2R,5S)-1-[(tert-butoxy) carbonyl 1-5-[2-(4-chloro-3-fluorophenoxy) acetamido] piperidine-2-carboxylic acid (Intermediate 3) and 2-amino-5-(difluoro-methoxy) phenol (Intermediate 4) | M/Z: 470, 472 [M + H]$^+$, ESI$^+$, RT = 2.22 (S4). | 1H NMR (500 MHz, DMSO-d$_6$) δ 8.00 (d, J = 8.1 Hz, 1H), 7.76 (d, J = 8.7 Hz, 1H), 7.64 (d, J = 2.3 Hz, 1H), 7.51 (t, J = 8.9 Hz, 1H), 7.43-7.18 (m, 2H), 7.09 (dd, J = 11.4, 2.8 Hz, 1H), 6.90-6.83 (m, 1H), 4.54 (s, 2H), 3.98-3.91 (m, 1H), 3.81-3.69 (m, 1H), 3.09-3.02 (m, 1H), 2.95-2.84 (m, 1H), 2.20-2.06 (m, 1H), 1.95 (d, J = 12.9 Hz, 1H), 1.84-1.71 (m, 1H), 1.64-1.50 (m, 1H). |

Scheme for route 6

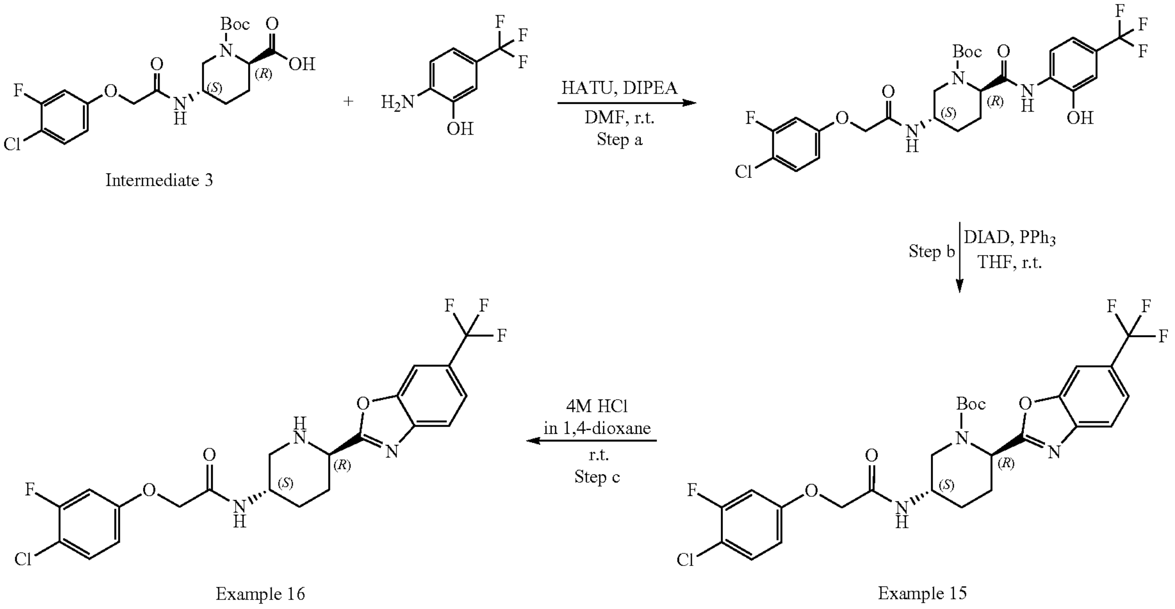

Step 6.a: tert-butyl (2R,5S)-5-[2-(4-chloro-3-fluorophenoxy)acetamido]-2-{[2-hydroxy-4-(trifluoromethyl)phenyl]carbamoyl}piperidine-1-carboxylate

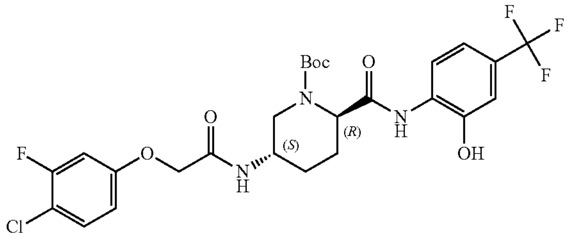

To a solution of 2-amino-5-(trifluoromethyl)phenol (164 mg, 0.928 mmol), DIPEA (0.49 mL, 2.79 mmol) and (2R,55)-1-[(tert-butoxy)carbonyl]-5-[2-(4-chloro-3-fluorophenoxy) acetamido]piperidine-2-carboxylic acid (Intermediate 3, 400 mg, 0.928 mmol) in anhydrous DMF (8 mL) was added HATU (353 mg, 0.928 mmol) and the mixture was stirred at r.t. for 2 h. The reaction mixture was diluted with EtOAc (30 mL) and washed with $H_2O$ (2×20 mL). The combined organic extracts were dried over $MgSO_4$, concentrated in vacuo, and purified by FCC on silica gel (10-100% EtOAc in heptane) to afford the title compound (53% purity, 507 mg, 0.456 mmol, 49% yield) as a colourless oil; M/Z: 590, 592 $[M+H]^+$, $ESI^+$, RT=4.19 min (S4).

Example 15 (Step 6.b): tert-butyl (2R,5S)-5-[2-(4-chloro-3-fluorophenoxy)acetamido]-2-[6-(trifluoromethyl)-1,3-benzoxazol-2-yl]piperidine-1-carboxylate Example 15

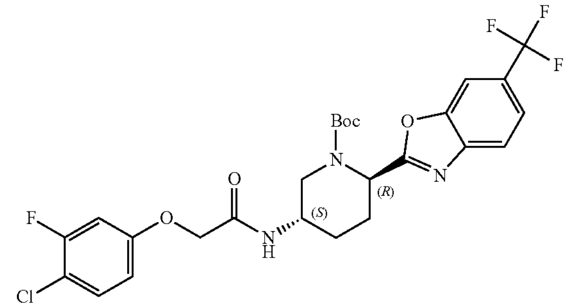

To a solution of tert-butyl (2R,5S)-5-[2-(4-chloro-3-fluorophenoxy)acetamido]-2-{[2-hydroxy-4-(trifluoromethyl) phenyl]carbamoyl}piperidine-1-carboxylate (53% purity, 507 mg, 0.456 mmol) and DIAD (0.11 mL, 0.547 mmol) in anhydrous THF (6 mL) at 0° C., was added $PPh_3$ (155 mg, 0.592 mmol) and the mixture was stirred at rt for 4 h. The reaction mixture was diluted with EtOAc (10 mL) and washed with $H_2O$ (2×10 mL). The organic extracts were dried over $MgSO_4$, concentrated in vacuo and purified by FCC on silica gel (0-100% EtOAc in heptane) to afford the title compound (54% purity, 430 mg, 0.406 mmol, 89% yield) as a white solid; $^1$H NMR (400 MHz, DMSO) δ 8.25 (s, 1H), 8.13 (d, J=7.1 Hz, 1H), 7.98 (d, J=8.3 Hz, 1H), 7.75 (d, J=8.3 Hz, 1H), 7.49 (t, J=8.9 Hz, 1H), 7.06 (dd, J=11.4, 2.8 Hz, 1H), 6.84 (dd, J=9.0, 2.0 Hz, 1H), 5.75 (s, 2H), 4.64-4.54 (m, 2H), 4.03-3.87 (m, 2H), 2.35-2.18 (m, 2H), 1.80-1.64 (m, 2H), 1.39-1.34 (m, 9H); M/Z: 472, 474 $[M-Boc+H]^+$, $ESI^+$, RT=1.17 min (S2).

Example 16 (Step 6.c): 2-(4-chloro-3-fluorophenoxy)-N-[(3S,6R)-6-[6-(trifluoromethyl)-1,3-benzoxazol-2-yl]piperidin-3-yl]acetamide Example 16

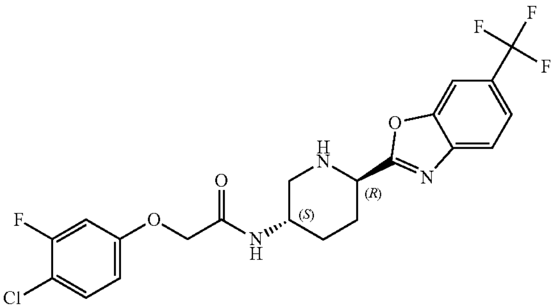

tert-butyl (2R,55)-5-[2-(4-chloro-3-fluorophenoxy)acetamido]-2-[6-(trifluoromethyl)-1,3-benzoxazol-2-yl]piperidine-1-carboxylate (Example 15, 54% purity, 430 mg, 0.406 mmol) was dissolved in 4 M HCl in 1,4-dioxane (5 mL) and stirred at r.t. for 3 h. The reaction mixture was diluted with EtOAc (30 mL) and washed with satd aq $NaHCO_3$ solution. The organic extracts were dried over $MgSO_4$, concentrated in vacuo and purified by prep. HPLC (Method 3) to afford the title compound (90 mg, 0.186 mmol, 46% yield) as a white solid; $^1$H NMR (400 MHz, DMSO-$d_6$) δ 8.21 (s, 1H), 7.97 (dd, J=19.4, 8.2 Hz, 2H), 7.73 (dd, J=8.3, 1.2 Hz, 1H), 7.50 (t, J=8.9 Hz, 1H), 7.08 (dd, J=11.4, 2.8 Hz, 1H), 6.86 (ddd, J=9.0, 2.8, 1.0 Hz, 1H), 4.54 (s, 2H), 4.05-3.96 (m, 1H), 3.82-3.70 (m, 1H), 3.11-3.03 (m, 1H), 2.94 (s, 1H), 2.56-2.52 (m, 1H), 2.19-2.09 (m, 1H), 2.00-1.91 (m, 1H), 1.85-1.51 (m, 2H); M/Z: 472, 474 $[M+H]^+$, $ESI^+$, RT=2.31 min (S4).

The example compounds in Table 2 were synthesised according to general route 6 as exemplified by Examples 15 and 16 using the corresponding intermediates.

TABLE 2

| Ex | Structure | Name | Intermediates | LCMS data | $^1$H NMR |
|---|---|---|---|---|---|
| 17 | 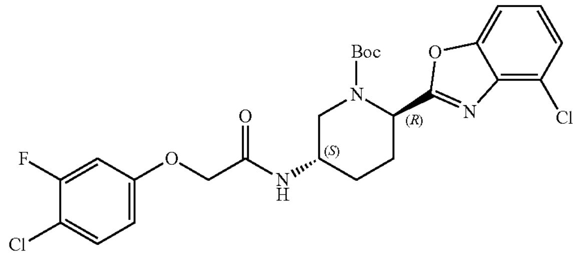 | tert-butyl (2R,5S)-2-(4-chloro-1,3-benzoxazol-2-yl)-5-[2-(4-chloro-3-fluorophenoxy) acetamido] piperidine-1-carboxylate | (2R,5S)-1-[(tert-butoxy) carbonyl]-5-[2-(4-chloro-3-fluorophenoxy) acetamido] piperidine-2-carboxylic acid (Intermediate 3) and 2-amino-3-chlorophenol | M/Z: 538, 540 [M + H]$^+$, ESI$^+$, RT = 4.37 (S4). | |
| 18 | 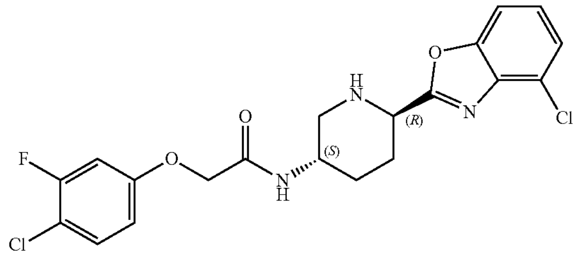 | N-[(3S,6R)-6-(4-chloro-1,3-benzoxazol-2-yl)piperidin-3-yl]-2-(4-chloro-3-fluorophenoxy) acetamide | (2R,5S)-1-[(tert-butoxy) carbonyl 1-5-[2-(4-chloro-3-fluorophenoxy) acetamido] piperidine-2-carboxylic acid (Intermediate 3) and 2-amino-3-chlorophenol | M/Z: 438, 440 [M + H]$^+$, ESI$^+$, RT = 2.18 (S4). | $^1$H NMR(500 MHz, DMSO-$d_6$) δ 8.01 (d, J = 8.1 Hz, 1H), 7.72 (d, J = 8.1 Hz, 1H), 7.55-7.38 (m, 3H), 7.09 (dd, J = 11.4, 2.8 Hz, 1H), 6.90-6.84 (m, 1H), 4.55 (s, 2H), 4.02-3.95 (m, 1H), 3.81-3.71 (m, 1H), 3.07 (d, J = 11.9 Hz, 1H), 2.99-2.93 (m, 1H), 2.53-2.52 (m, 1H), 2.17-2.10 (m, 1H), 1.99-1.92 (m, 1H), 1.83-1.74 (m, 1H), 1.63-1.52 (m, 1H). |

Scheme for route 7

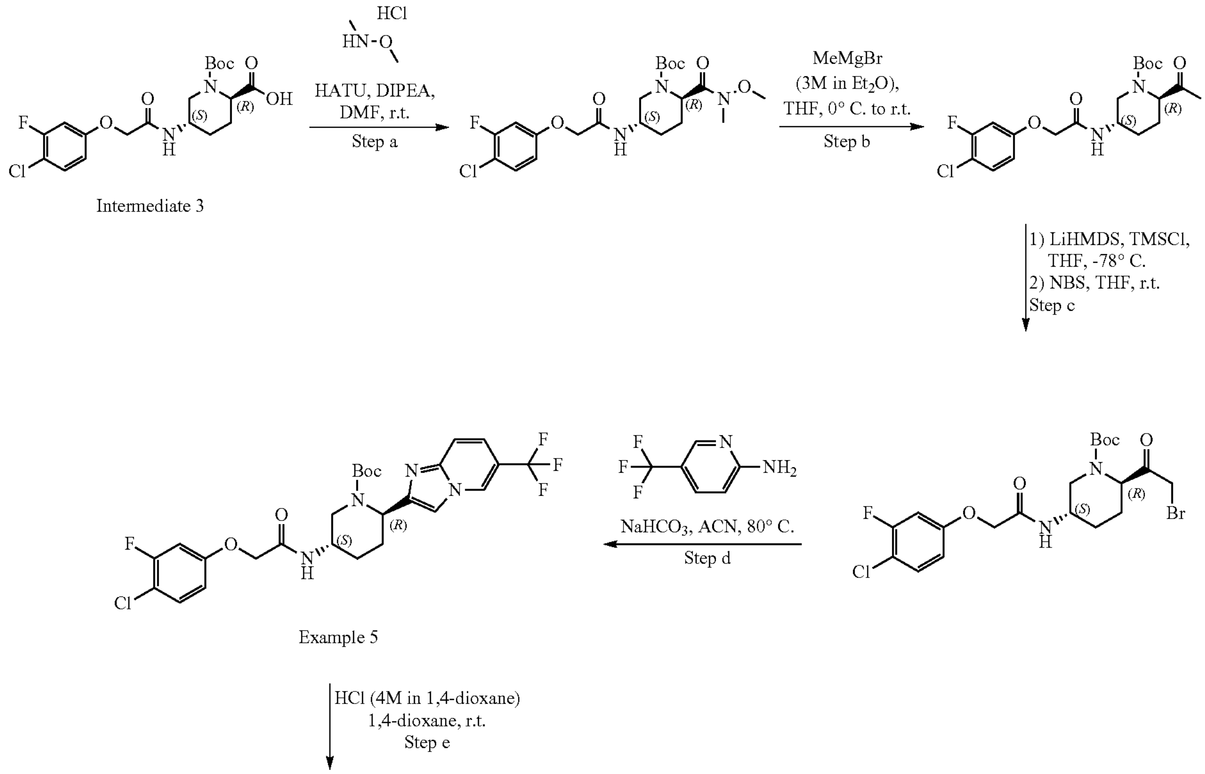

Intermediate 3

Example 5

-continued

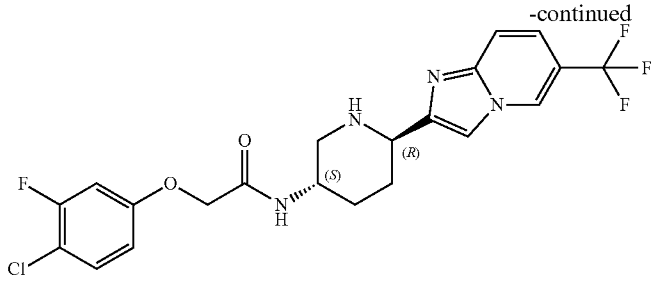

Example 6

Step 7.a: tert-butyl (2R,5S)-5-[[2-(4-chloro-3-fluoro-phenoxy)acetyl]amino]-2-[methoxy(methyl)carbamoyl]piperidine-1-carboxylate

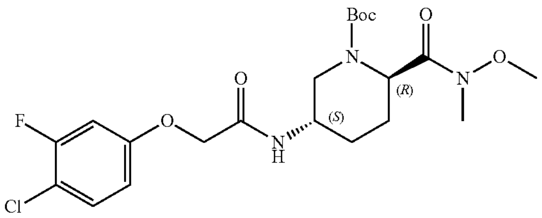

To a solution of N-methoxymethanamine; hydrochloride (340 mg, 3.48 mmol), DIPEA (1.8 mL, 10.4 mmol) and (2R,5S)-1-[(tert-butoxy)carbonyl]-5-[2-(4-chloro-3-fluoro-phenoxy) acetamido]piperidine-2-carboxylic acid (1.50 g, 3.48 mmol, Intermediate 3) in DMF (anhydrous, 49.2 mL) was added HATU (1324 mg, 3.48 mmol) and the reaction mixture was stirred at r.t. for 3 h. The reaction mixture was diluted with $H_2O$ (20 mL) and extracted with EtOAc (2×30 mL). The combined organic layers were dried ($Na_2SO_4$) and concentrated in vacuo to afford the title compound (95% purity, 1.58 g, 3.17 mmol, 91% yield) as a colourless oil. The product was used in the next reaction without any further purification; $^1H$ NMR (500 MHz, $CDCl_3$) δ 7.31 (t, J=8.6 Hz, 1H), 6.74 (dd, J=10.3, 2.8 Hz, 2H), 6.66 (ddd, J=8.9, 2.8, 1.1 Hz, 1H), 5.17-4.83 (m, 1H), 4.45 (s, 2H), 4.23-4.17 (m, 1H), 3.98-3.61 (m, 5H), 3.18 (s, 3H), 1.95-1.81 (m, 4H), 1.41 (s, 9H); M/Z: 496 $[M+Na]^+$, $ESI^+$, RT=0.94 min (S2).

Step 7.b: tert-butyl (2R,5S)-2-acetyl-5-[[2-(4-chloro-3-fluoro-phenoxy) acetyl]amino]piperidine-1-carboxylate

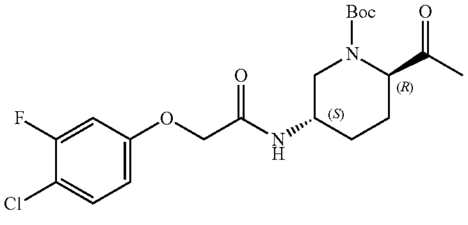

To a solution of tert-butyl (2R,5S)-5-[[2-(4-chloro-3-fluoro-phenoxy)acetyl]amino]-2-[methoxy(methyl)carbamoyl]piperidine-1-carboxylate (1.58 g, 3.17 mmol) in THF (anhydrous, mL) at 0° C. was added 3 M MeMgBr (3 M in $Et_2O$) (1.4 mL, 4.12 mmol). The reaction was warmed to r.t. over 1 h. The reaction mixture was diluted with EtOAc and the organic layer was washed with satd aq $NH_4Cl$ (3×). The organic layer was dried ($MgSO_4$) and concentrated in vacuo. Purification by FCC on silica gel (10-100% EtOAc in heptane) afforded the title compound (89% purity, 622 mg, 1.29 mmol, 41% yield) as a pale yellow oil; $^1H$ NMR (400 MHz, $CDCl_3$) δ 7.32 (t, J=8.6 Hz, 1H), 6.87-6.63 (m, 3H), 4.85-4.53 (m, 1H), 4.48-4.41 (m, 2H), 4.15-4.08 (m, 1H), 2.17 (s, 3H), 2.15-2.06 (m, 1H), 1.84-1.56 (m, 5H), 1.45 (s, 9H); M/Z: 429 $[M+H]^+$, $ESI^+$, RT=3.46 min (S4).

Step 7.c: tert-butyl (2R,5S)-2-(2-bromoacetyl)-5-[[2-(4-chloro-3-fluoro-phenoxy)acetyl]amino]piperidine-1-carboxylate

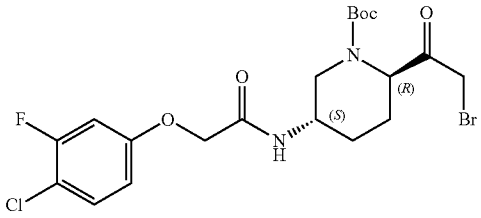

To a solution of tert-butyl (2R,5S)-2-acetyl-5-[[2-(4-chloro-3-fluoro-phenoxy)acetyl]amino]piperidine-1-carboxylate (89% purity, 431 mg, 0.894 mmol) in THF (anhydrous, 8 mL) at −78° C. was added 1 M LiHMDS in THF (2.7 mL, 2.68 mmol) and the reaction was stirred for 30 min. TMSCl (0.34 mL, 2.68 mmol) was added and the mixture stirred at −78° C. for 30 min. A solution of NBS (239 mg, 1.34 mmol) in THF (anhydrous, 4 mL) was added and the mixture was stirred at r.t. for 2 h. The mixture was diluted with EtOAc (20 mL) and washed with satd aq $NH_4Cl$ (2×20 mL). The combined organic layers were dried ($MgSO_4$) and evaporated to dryness. Purification by FCC on silica gel (10-100% EtOAc in heptane) afforded the title compound (39% purity, 482 mg, 0.370 mmol, 41% yield) as a yellow oil. The product was used in the next reaction without further purification; M/Z: 407, 409 $[M-Boc+H]^+$, $ESI^+$, RT=3.78 min (S4).

Example 5 (Step 7.d): tert-butyl (2R,5S)-5-[[2-(4-chloro-3-fluoro-phenoxy)acetyl]amino]-2-[6-(trifluoromethyflimidazo[1,2-a]pyridin-2-yl]piperidine-1-carboxylate Example 5

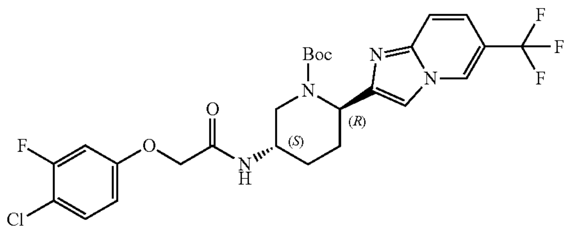

A solution of 2-amino-5-(trifluoromethyl)pyridine (27 mg, 0.165 mmol), tert-butyl (2R,5S)-2-(2-bromoacetyl)-5-[[2-(4-chloro-3-fluoro-phenoxy)acetyl]amino]piperidine-1-carboxylate (39%, 215 mg, 0.165 mmol) and $NaHCO_3$ (14 mg, 0.165 mmol) in ACN (anhydrous, 2.15 mL) was stirred at 80° C. for 6 h. The reaction was cooled to r.t. and diluted with EtOAc. The organic layer was washed with water and brine, dried ($MgSO_4$) and concentrated in vacuo to afford the title compound (35% purity, 240 mg, 0.147 mmol, 89% yield) as an orange oil. The product was used in the next reaction without further purification; M/Z: 571 $[M+H]^+$, $ESI^+$, RT=3.71 min (S4).

Example 6 (Step 7.e): 2-(4-chloro-3-fluoro-phenoxy)-N-[(3S,6R)-6-[6-(trifluoromethyl)imidazo[1,2-a]pyridin-2-yl]-3-piperidyl]acetamide Example 6

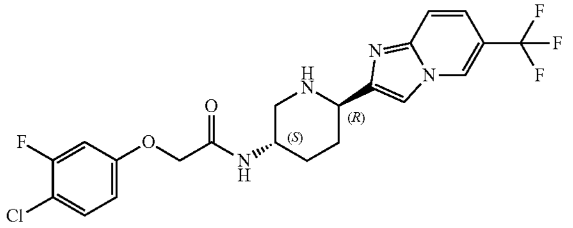

To a solution of tert-butyl (2R,5S)-5-[[2-(4-chloro-3-fluoro-phenoxy)acetyl]amino]-2-[6-(trifluoromethyl)imidazo[1,2-a]pyridin-2-yl]piperidine-1-carboxylate (35% purity, 240 mg, 0.147 mmol, Example 5) in 1,4-dioxane (2 mL) was added HCl (4 M in 1,4-dioxane) (2.0 mL, 8.00 mmol) and the reaction was stirred at r.t. for 16 h. The reaction was diluted with EtOAc and washed with satd aq $NaHCO_3$ (2×). The organic phase was dried ($MgSO_4$) and evaporated in vacuo. Purification by prep. HPLC (Method 3) afforded the title compound (95% purity, 7.9 mg, 0.0159 mmol, 11% yield) as an off-white amorphous solid; $^1H$ NMR (400 MHz, DMSO-$d_6$) δ 8.76 (d, J=7.2 Hz, 1H), 8.09-7.96 (m, 3H), 7.51 (t, J=8.9 Hz, 1H), 7.16 (dd, J=7.1, 1.7 Hz, 1H), 7.08 (dd, J=11.4, 2.8 Hz, 1H), 6.87 (dd, J=8.9, 1.9 Hz, 1H), 4.54 (s, 2H), 3.97-3.76 (m, 2H), 3.17-3.08 (m, 1H), 2.71-2.59 (m, 1H), 2.21-2.11 (m, 1H), 2.04-1.88 (m, 2H), 1.71-1.54 (m, 2H); M/Z: 471 $[M+H]^+$, $ESI^+$, RT=2.08 min (S4).

The example compounds in Table 3 were synthesised according to general route 7 as exemplified by Examples 5 and 6 using the corresponding intermediates.

TABLE 3

| Ex | Structure | Name | Intermediates | LCMS data | $^1H$ NMR |
|---|---|---|---|---|---|
| 7 | 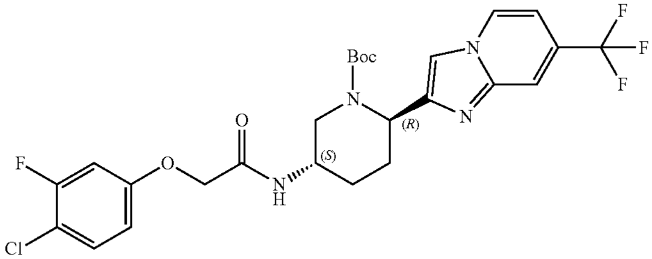 | tert-butyl (2R,5S)-5-[2-(4-chloro-3-fluoro-phenoxy) acetamido]-2-[7-(trifluoro-methyl) imidazo [1,2-a] pyridin-2 yl] piperidine-1-carboxylate | (2R,5S)-1-[(tert-butoxy) carbon yl]-5-[2-(4-chloro-3-fluoro-phenoxy) acetamido] piperidine-2-carboxylic acid (Intermediate 3) and 4-(trifluoro-methyl) pyridin-2-amine | M/Z: 571 [M + H]$^+$, ESI$^+$, RT = 3.82, 48% purity (S4). | |

TABLE 3-continued

| Ex | Structure | Name | Intermediates | LCMS data | $^1$H NMR |
|---|---|---|---|---|---|
| 8 | 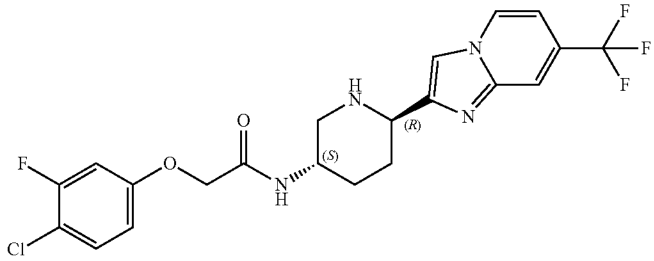 | 2-(4-chloro-3-fluoro-phenoxy)-N-[(3S,6R)-6-[7-(trifluoro-methyl)imidazo[1,2-a]pyridin-2-yl]-3-piperidyl]acetamide | (2R,5S)-1-[(tert-butoxy)carbonyl]-5-[2-(4-chloro-3-fluoro-phenoxy)acetamido]piperidine-2-carboxylic acid (Intermediate 3) and 4-(trifluoro-methyl)pyridin-2-amine | M/Z: 471 [M + H]$^+$, ESI$^+$, RT = 2.08 (S4). | $^1$H NMR (500 MHz, DMSO-$d_6$) δ 8.73 (d, J = 7.1 Hz, 1H), 8.01-7.93 (m, 3H), 7.50 (t, J = 8.9 Hz, 1H), 7.15-7.05 (m, 2H), 6.86 (ddd, J = 9.0, 2.8, 1.1 Hz, 1H), 4.53 (s, 2H), 3.80-3.68 (m, 2H), 3.11-3.05 (m, 1H), 2.79-2.65 (m, 1H), 2.54 2.52 (m, 1H), 2.14-2.08 (m, 1H), 1.96-1.85 (m, 1H), 1.59-1.44 (m, 2H). |

II Assays

HEK-ATF4 High Content Imaging assay

Example compounds were tested in the HEK-ATF4 High Content Imaging assay to assess their pharmacological potency to prevent Tunicamycin induced ISR. Wild-type HEK293 cells were plated in 384-well imaging assay plates at a density of 12,000 cells per well in growth medium (containing DMEM/F12, 10% FBS, 2 mM L-Glutamine, 100 U/mL Penicillin—100 μg/mL Streptomycin) and incubated at 37° C., 5% $CO_2$. 24 h later, the medium was changed to 50 μL assay medium per well (DMEM/F12, 0.3% FBS, 2 mM L-Glutamine, 100 U/mL Penicillin—100 μg/mL Streptomycin). Example compounds were serially diluted in DMSO, spotted into intermediate plates and prediluted with assay medium containing 3.3 μM Tunicamycin to give an 11-fold excess of final assay concentration. In addition to the example compound testing area, the plates also contained multiples of control wells for assay normalization purposes, wells containing Tunicamycin but no example compounds (High control), as well as wells containing neither example compound nor Tunicamycin (Low control). The assay was started by transferring 5 μL from the intermediate plate into the assay plates, followed by incubation for 6 h at 37° C., 5% $CO_2$. Subsequently, cells were fixed (4% PFA in PBS, 20 min at r.t.) and submitted to indirect ATF4 immunofluorescence staining (primary antibody rabbit anti ATF4, clone D4B8, Cell Signaling Technologies; secondary antibody Alexa Fluor 488 goat anti-rabbit IgG (H+L), Thermofisher Scientific). Nuclei were stained using Hoechst dye (Thermofisher Scientific), and plates were imaged on an Opera Phenix High Content imaging platform equipped with 405 nm and 488 nm excitation. Finally, images were analyzed using script based algorithms. The main readout HEK-ATF4 monitored the ATF4 signal ratio between nucleus and cytoplasm. Tunicamycin induced an increase in the overall ATF4 ratio signal, which was prevented by ISR modulating example compounds. In addition, HEK-CellCount readout was derived from counting the number of stained nuclei corresponding to healthy cells. This readout served as an internal toxicity control. The example compounds herein did not produce significant reduction in CellCount.

HEK ATF4 Activity of the tested example compounds is provided in Table 4 as follows: +++=$IC_{50}$ 1-500 nM; ++=$IC_{50}$>500-2000 nM; +=$IC_{50}$>2000-15000 nM.

TABLE 4

| Example number | HEK-ATF4 Activity |
|---|---|
| 2 | ++ |
| 4 | + |
| 6 | + |
| 8 | + |
| 10 | ++ |
| 12 | +++ |
| 14 | ++ |
| 16 | +++ |
| 18 | + |

REFERENCES (1) Pakos-Zebrucka K, Koryga I, Mnich K, Ljujic M, Samali A, Gorman A M. The integrated stress response. EMBO Rep. 2016 October; 17(10):1374-1395. Epub 2016 Sep. 14.

(2) Wek R C, Jiang H Y, Anthony T G. Coping with stress: eIF2 kinases and translational control. Biochem Soc Trans. 2006 February; 34(Pt 1):7-11.

(3) Donnelly N, Gorman A M, Gupta S, Samali A. The eIF2alpha kinases: their structures and functions. Cell Mol Life Sci. 2013 October; 70(19):3493-511

(4) Jackson R J, Hellen C U, Pestova T V. The mechanism of eukaryotic translation initiation and principles of its regulation. Nat Rev Mol Cell Biol. 2010 February; 11(2):113-27

(5) Lomakin I B, Steitz T A. The initiation of mammalian protein synthesis and mRNA scanning mechanism. Nature. 2013 Aug. 15; 500(7462):307-11

(6) Pain V M. Initiation of protein synthesis in eukaryotic cells. Eur J Biochem. 1996 Mar. 15; 236(3):747-71

(7) Pavitt G D. Regulation of translation initiation factor eIF2B at the hub of the integrated stress response. Wiley Interdiscip Rev RNA. 2018 November; 9(6):e1491.

(8) Krishnamoorthy T, Pavitt G D, Zhang F, Dever T E, Hinnebusch A G. Tight binding of the phosphorylated alpha subunit of initiation factor 2 (eIF2alpha) to the regulatory subunits of guanine nucleotide exchange factor eIF2B is required for inhibition of translation initiation. Mol Cell Biol. 2001 August; 21(15):5018-30.

(9) Hinnebusch, A. G., Ivanov, I. P., & Sonenberg, N. (2016). Translational control by 5'-untranslated regions of eukaryotic mRNAs. Science, 352(6292), 1413-1416.

(10) Young, S. K., & Wek, R. C. (2016). Upstream open reading frames differentially regulate gene-specific translation in the integrated stress response. The Journal of Biological Chemistry, 291(33), 16927-16935.

(11) Lin J H, Li H, Zhang Y, Ron D, Walter P (2009) Divergent effects of PERK and IRE1 signaling on cell viability. PLoS ONE 4: e4170

(12) Tabas I, Ron D. Nat Cell Biol. 2011 March; 13(3):184-90. Integrating the mechanisms of apoptosis induced by endoplasmic reticulum stress.

(13) Shore G C, Papa F R, Oakes S A. Curr Opin Cell Biol. 2011 April; 23(2):143-9. Signaling cell death from the endoplasmic reticulum stress response.

(14) Bi M, Naczki C, Koritzinsky M, Fels D, Blais J, Hu N, Harding H, Novoa I, Varia M, Raleigh J, Scheuner D, Kaufman R J, Bell J, Ron D, Wouters B G, Koumenis C. EMBO J. 2005 Oct. 5; 24(19):3470-81 ER stress-regulated translation increases tolerance to extreme hypoxia and promotes tumor growth.

(15) Bobrovnikova-Marjon E, Grigoriadou C, Pytel D, Zhang F, Ye J, Koumenis C, Cavener D, Diehl J A. Oncogene. 2010 Jul. 8; 29(27):3881-95 PERK promotes cancer cell proliferation and tumor growth by limiting oxidative DNA damage.

(16) Avivar-Valderas A, Salas E, Bobrovnikova-Marjon E, Diehl J A, Nagi C, Debnath J, Aguirre-Ghiso J A. Mol Cell Biol. 2011 September; 31(17):3616-29. PERK integrates autophagy and oxidative stress responses to promote survival during extracellular matrix detachment.

(17) Blais, J. D.; Addison, C. L.; Edge, R.; Falls, T.; Zhao, H.; Kishore, W.; Koumenis, C.; Harding, H. P.; Ron, D.; Holcik, M.; Bell, J. C. Mol. Cell. Biol. 2006, 26, 9517-9532. PERK-dependent translational regulation promotes tumor cell adaptation and angiogenesis in response to hypoxic stress.

(18) Taalab Y M, Ibrahim N, Maher A, Hassan M, Mohamed W, Moustafa A A, Salama M, Johar D, Bernstein L. Rev Neurosci. 2018 Jun. 27; 29(4):387-415. Mechanisms of disordered neurodegenerative function: concepts and facts about the different roles of the protein kinase RNA-like endoplasmic reticulum kinase (PERK).

(19) Remondelli P, Renna M. Front Mol Neurosci. 2017 Jun. 16; 10:187. The Endoplasmic Reticulum Unfolded Protein Response in Neurodegenerative Disorders and Its Potential Therapeutic Significance.

(20) Halliday M, Mallucci G R. Neuropathol Appl Neurobiol. 2015 June; 41(4):414-27. Review: Modulating the unfolded protein response to prevent neurodegeneration and enhance memory.

(21) Halliday M, Radford H, Sekine Y, Moreno J, Verity N, le Quesne J, Ortori C A, Barrett D A, Fromont C, Fischer P M, Harding H P, Ron D, Mallucci G R. Cell Death Dis. 2015 Mar. 5; 6:e1672. Partial restoration of protein synthesis rates by the small molecule ISRIB prevents neurodegeneration without pancreatic toxicity.

(22) Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R. Nature 2012; 485: 507-11. Sustained translational repression by eIF2alpha-P mediates prion neurodegeneration.

(23) Skopkova M, Hennig F, Shin B S, Turner C E, Stanikova D, Brennerova K, Stanik J, Fischer U, Henden L, Muller U, Steinberger D, Leshinsky-Silver E, Bottani A, Kurdiova T, Ukropec J, Nyitrayova O, Kolnikova M, Klimes I, Borck G, Bahlo M, Haas S A, Kim J R, Lotspeich-Cole L E, Gasperikova D, Dever T E, Kalscheuer V M. Hum Mutat. 2017 April; 38(4):409-425. EIF2S3 Mutations Associated with Severe X-Linked Intellectual Disability Syndrome MEHMO.

(24) Hamilton E M C, van der Lei H D W, Vermeulen G, Gerver J A M, Lourenco C M, Naidu S, Mierzewska H, Gemke R J B J, de Vet H C W, Uitdehaag B M J, Lissenberg-Witte B I; VWM Research Group, van der Knaap M S. Ann Neurol. 2018 August; 84(2):274-288. Natural History of Vanishing White Matter.

(25) Bugiani M, Vuong C, Breur M, van der Knaap M S. Brain Pathol. 2018 May; 28(3):408-421. Vanishing white matter: a leukodystrophy due to astrocytic dysfunction.

(26) Wong Y L, LeBon L, Edalji R, Lim H B, Sun C, Sidrauski C. Elife. 2018 Feb. 28; 7. The small molecule ISRIB rescues the stability and activity of Vanishing White Matter Disease eIF2B mutant complexes.

(27) Wong Y L, LeBon L, Basso A M, Kohlhaas K L, Nikkel A L, Robb H M, Donnelly-Roberts D L, Prakash J, Swensen A M, Rubinstein N D, Krishnan S, McAllister F E, Haste N V, O'Brien J J, Roy M, Ireland A, Frost J M, Shi L, Riedmaier S, Martin K, Dart M J, Sidrauski C. Elife. 2019 Jan. 9; 8. eIF2B activator prevents neurological defects caused by a chronic integrated stress response.

(28) Nguyen H G, Conn C S, Kye Y, Xue L, Forester C M, Cowan J E, Hsieh A C, Cunningham J T, Truillet C, Tameire F, Evans M J, Evans C P, Yang J C, Hann B, Koumenis C, Walter P, Carroll P R, Ruggero D. Sci Transl Med. 2018 May 2; 10(439). Development of a stress response therapy targeting aggressive prostate cancer.

(29) Waring M, Expert Opinion on Drug Discovery Volume 5, 2010—Issue 3, 235-248. Lipophilicity in Drug Discovery.

(30) Alelyunas Y W, et. al. Bioorg. Med. Chem. Lett., 20(24) 2010, 7312-7316. Experimental solubility profiling of marketed CNS drugs, exploring solubility limit of CNS discovery candidate.

(31) Redfern W S, et. al., Cardiovascular Research 58(2003), 32-45. Relationships between preclinical cardiac electrophysiology, clinical QT interval prolongation and torsade de pointes for a broad range of drugs.

The invention claimed is:

1. A compound of formula (I)

(I)

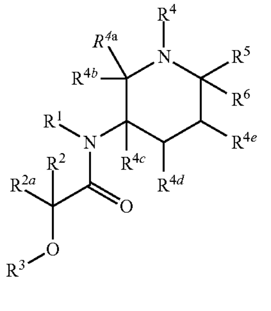

or a pharmaceutically acceptable salt, tautomer or stereoisomer thereof, wherein:

$R^1$ is H or $C_{1-4}$ alkyl, wherein $C_{1-4}$ alkyl is optionally substituted with one or more halogen, which are the same or different;

$R^2$ is H, F or $C_{1-4}$ alkyl, wherein $C_{1-4}$ alkyl is optionally substituted with one or more halogen, which are the same or different;

$R^{2a}$ is H;

$R^3$ is phenyl or 6 membered aromatic heterocyclyl, wherein $R^3$ is optionally substituted with one or more $R^7$, which are the same or different;

$R^7$ is halogen, CN, $C(O)OR^8$, $OR^8$, $C(O)R^8$, $C(O)N(R^8R^{8a})$, $S(O)_2N(R^8R^{8a})$, $S(O)N(R^8R^{8a})$, $S(O)_2R^8$, $S(O)R^8$, $N(R^8)S(O)_2N(R^{8a}R^{8b})$, $SR^8$, $N(R^8R^{8a})$, $NO_2$, $OC(O)R^8$, $N(R^8)C(O)R^{8a}$, $N(R^8)S(O)_2R^{8a}$, $N(R^8)S(O)R^{8a}$, $N(R^8)C(O)OR^{8a}$, $N(R^8)C(O)N(R^{8a}R^{8b})$, $OC(O)N(R^8R^{8a})$, $C_{1-6}$ alkyl, $C_{2-6}$ alkenyl or $C_{2-6}$ alkynyl, wherein $C_{1-6}$ alkyl, $C_{2-6}$ alkenyl and $C_{2-6}$ alkynyl are optionally substituted with one or more $R^9$, which are the same or different;

$R^8$, $R^{8a}$, $R^{8b}$ are independently selected from the group consisting of H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl are optionally substituted with one or more halogen, which are the same or different;

$R^9$ is halogen, CN, $C(O)OR^{10}$, $OR^{10}$, $C(O)R^{10}$, $C(O)N(R^{10}R^{10a})$, $S(O)_2N(R^{10}R^{10a})$, $S(O)N(R^{10}R^{10a})$, $S(O)_2R^{10}$, $S(O)R^{10}$, $N(R^{10})S(O)_2N(R^{10a}R^{10b})$, $SR^{10}$, $N(R^{10}R^{10a})$, $NO_2$, $OC(O)R^{10}$, $N(R^{10})C(O)R^{10a}$, $N(R^{10})SO_2R^{10a}$, $N(R^{10})S(O)R^{10a}$, $N(R^{10})C(O)N(R^{10a}R^{10b})$, $N(R^{10})C(O)OR^{10a}$ or $OC(O)N(R^{10}R^{10a})$;

$R^{10}$, $R^{10a}$, $R^{10b}$ are independently selected from the group consisting of H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl are optionally substituted with one or more halogen, which are the same or different;

$R^4$ is H, $C(O)OC_{1-4}$ alkyl or $C_{1-4}$ alkyl, wherein $C(O)OC_{1-4}$ alkyl and $C_{1-4}$ alkyl are optionally substituted with one or more substituents selected from the group consisting of halogen, OH and O—$C_{1-3}$ alkyl, wherein the substituents are the same or different;

$R^{4a}$, $R^{4b}$, $R^{4c}$, $R^5$ are independently selected from the group consisting of H, halogen and $C_{1-4}$ alkyl; and $R^{4d}$, $R^{4e}$ are independently selected from the group consisting of H, OH, $OC_{1-4}$ alkyl, halogen and $C_{1-4}$ alkyl;

or $R^4$ and one of $R^{4d}$ and $R^{4e}$ form a methylene or ethylene group;

or $R^4$ and $R^{4c}$ form an ethylene group;

or $R^{4b}$ and $R^{4d}$ form a covalent single bond;

$R^6$ is 7 to 12 membered heterobicyclyl, wherein $R^6$ is optionally substituted with one or more $R^{11}$, which are the same or different;

$R^{11}$ is $R^{12}$, OH, $OR^{12}$, halogen or CN;

$R^{12}$ is cyclopropyl, $C_{1-6}$ alkyl, $C_{2-6}$ alkenyl or $C_{2-6}$ alkynyl, wherein $R^{12}$ is optionally substituted with one or more $R^{13}$, which are the same or different;

$R^{13}$ is halogen, CN or $OR^{14}$; and $R^{14}$ is H or $C_{1-4}$ alkyl, wherein $C_{1-4}$ alkyl is optionally substituted with one or more halogen, which are the same or different.

2. The compound of claim 1 or a pharmaceutically acceptable salt, tautomer or stereoisomer thereof, wherein $R^4$ is H, $CH_3$, $CH_2CH_3$, or $CH_2CH_2OCH_3$.

3. The compound of claim 1 or a pharmaceutically acceptable salt, tautomer or stereoisomer thereof, wherein $R^{4a}$, $R^{4b}$, $R^{4c}$, $R^5$ are independently selected from the group consisting of H, halogen and $C_{1-4}$ alkyl and $R^{4d}$, $R^{4e}$ are independently selected from the group consisting of H, OH, $OC_{1-4}$ alkyl, halogen and $C_{1-4}$ alkyl.

4. The compound of claim 1 or a pharmaceutically acceptable salt, tautomer or stereoisomer thereof, wherein $R^1$ is H or $CH_3$.

5. The compound of claim 1 or a pharmaceutically acceptable salt, tautomer or stereoisomer thereof, wherein $R^2$ is H, F or $CH_3$.

6. The compound of claim 1 or a pharmaceutically acceptable salt, tautomer or stereoisomer thereof, wherein $R^1$, $R^2$, $R^{2a}$, $R^4$, $R^{4a}$, $R^{4b}$, $R^{4c}$, $R^5$, $R^{4d}$, $R^{4e}$ in formula (I) are H to give formula (Ia):

(Ia)

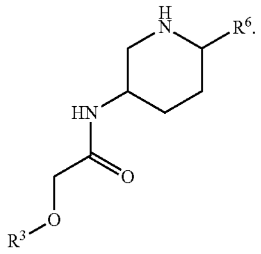

7. The compound of claim 1 or a pharmaceutically acceptable salt, tautomer or stereoisomer thereof, wherein $R^3$ is phenyl or pyridyl wherein $R^3$ is optionally substituted with one or more $R^7$, which are the same or different.

8. The compound of claim 1 or a pharmaceutically acceptable salt, tautomer or stereoisomer thereof, wherein $R^3$ is substituted with one, two or three $R^7$, which are the same or different.

9. The compound of claim 1 or a pharmaceutically acceptable salt, tautomer or stereoisomer thereof, wherein $R^7$ is F, Cl, Br, CN, $CHF_2$, $CF_3$, $OCH_3$, $OCF_3$, CH═O, $CH_2OH$ or $CH_3$.

10. The compound of claim 1 or a pharmaceutically acceptable salt, tautomer or stereoisomer thereof, wherein $R^1$, $R^2$, $R^{2a}$, $R^3$, $R^4$, $R^{4a}$, $R^{4b}$, $R^{4c}$, $R^{4d}$, $R^{4e}$, $R^5$ in formula (I) are selected to give formula (Ib):

(Ib)

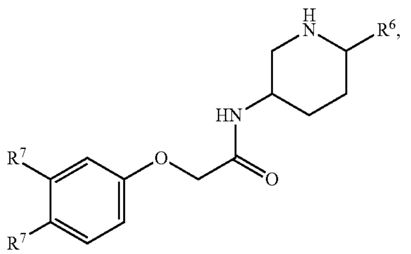

wherein each $R^7$ is independently selected from the group consisting of halogen and $CF_3$.

11. The compound of claim 1 or a pharmaceutically acceptable salt, tautomer or stereoisomer thereof, wherein $R^6$ is quinazolinyl, pyrrolo[1,2-a]pyrazinyl, 1,3-benzoxazolyl, pyrido[2,3-d]pyrimidinyl, pyrido[3,4-d]pyrimidinyl, pyrimido[5,4-d]pyrimidinyl, 1,2,3,4-tetrahydroquinolinyl, chromanyl, oxazolo[4,5-c]pyridinyl, imidazo[1,2-a]pyridinyl, [1,2,4]triazolo[1,5-a]pyridinyl, imidazo[1,2-b]pyridazinyl or 6,7-dihydro-4H-pyrano[4,3-d]oxazolyl, wherein $R^6$ is optionally substituted with one or more $R^{11}$, which are the same or different.

12. The compound of claim 1 or a pharmaceutically acceptable salt, tautomer or stereoisomer thereof, wherein $R^6$ is unsubstituted or substituted with one or two $R^{11}$, which are the same or different.

13. The compound of claim 1 or a pharmaceutically acceptable salt, tautomer or stereoisomer thereof, wherein $R^{11}$ is Cl, $CH_3$, $CF_3$, $CH_2CF_3$, $OCF_3$, $OCHF_2$ or $OCH_2CF_3$.

14. The compound of claim 1 or a pharmaceutically acceptable salt, tautomer or stereoisomer thereof, wherein $R^1$, $R^2$, $R^{2a}$, $R^4$, $R^{4a}$, $R^{4b}$, $R^{4c}$, $R^{4d}$, $R^{4e}$, $R^3$, $R^5$, $R^6$ in formula (I) are selected to give:

tert-butyl (2R,5S)-2-(6-chloro-1,3-benzoxazol-2-yl)-5-[2-(4-chloro-3-fluorophenoxy)acetamido]piperidine-1-carboxylate;

N-[(3S,6R)-6-(6-chloro-1,3-benzoxazol-2-yl)piperidin-3-yl]-2-(4-chloro-3-fluorophenoxy)acetamide;

tert-butyl (2R,5S)-2-(5-chloro-1,3-benzoxazol-2-yl)-5-[2-(4-chloro-3-fluorophenoxy)acetamido]piperidine-1-carboxylate;

N-[(3S,6R)-6-(5-chloro-1,3-benzoxazol-2-yl)piperidin-3-yl]-2-(4-chloro-3-fluorophenoxy)acetamide;

tert-butyl (2R,5S)-5-[[2-(4-chloro-3-fluoro-phenoxy)acetyl]amino]-2-[6-(trifluoromethyl)imidazo[1,2-a]pyridin-2-yl]piperidine-1-carboxylate;

2-(4-chloro-3-fluoro-phenoxy)-N-[(3S,6R)-6-[6-(trifluoromethyl)imidazo[1,2-a]pyridin-2-yl]-3-piperidyl]acetamide;

tert-butyl (2R,5S)-5-[2-(4-chloro-3-fluorophenoxy)acetamido]-2-[7-(trifluoromethyl)imidazo[1,2-a]pyridin-2-yl]piperidine-1-carboxylate or 2-(4-chloro-3-fluorophenoxy)-N-[(3S,6R)-6-[7-(trifluoromethyl)imidazo[1,2-a]pyridin-2-yl]-3-piperidyl]acetamide;

tert-butyl (2R,5S)-2-(7-chloro-1,3-benzoxazol-2-yl)-5-[2-(4-chloro-3-fluorophenoxy)acetamido]piperidine-1-carboxylate;

N-[(3S,6R)-6-(7-chloro-1,3-benzoxazol-2-yl)piperidin-3-yl]-2-(4-chloro-3-fluorophenoxy)acetamide;

tert-butyl (2R,5S)-5-[2-(4-chloro-3-fluorophenoxy)acetamido]-2-[6-(trifluoromethoxy)-1,3-benzoxazol-2-yl]piperidine-1-carboxylate;

2-(4-chloro-3-fluorophenoxy)-N-[(3S,6R)-6-[6-(trifluoromethoxy)-1,3-benzoxazol-2-yl]piperidin-3-yl]acetamide;

tert-butyl (2R,5S)-5-[2-(4-chloro-3-fluorophenoxy)acetamido]-2-[6-(difluoromethoxy)-1,3-benzoxazol-2-yl]piperidine-1-carboxylate;

2-(4-chloro-3-fluorophenoxy)-N-[(3S,6R)-6-[6-(difluoromethoxy)-1,3-benzoxazol-2-yl]piperidin-3-yl]acetamide;

tert-butyl (2R,5S)-5-[2-(4-chloro-3-fluorophenoxy)acetamido]-2-[6-(trifluoromethyl)-1,3-benzoxazol-2-yl]piperidine-1-carboxylate;

2-(4-chloro-3-fluorophenoxy)-N-[(3S,6R)-6-[6-(trifluoromethyl)-1,3-benzoxazol-2-yl]piperidin-3-yl]acetamide;

tert-butyl (2R,5S)-2-(4-chloro-1,3-benzoxazol-2-yl)-5-[2-(4-chloro-3-fluorophenoxy)acetamido]piperidine-1-carboxylate; or N-[(3S,6R)-6-(4-chloro-1,3-benzoxazol-2-yl)piperidin-3-yl]-2-(4-chloro-3-fluorophenoxy)acetamide.

15. The compound of claim 1 or a pharmaceutically acceptable salt, tautomer or stereoisomer thereof, wherein formula (I) has a stereochemistry as shown in formula (Ic):

(Ic)

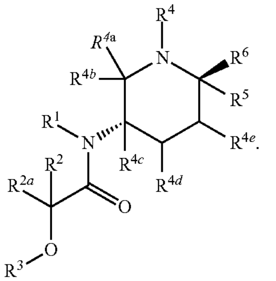

16. A pharmaceutical composition comprising at least one compound or a pharmaceutically acceptable salt, tautomer or stereoisomer thereof of claim 1 together with a pharmaceutically acceptable carrier, optionally in combination with one or more other bioactive compounds or pharmaceutical compositions.

17. A method of treating of one or more diseases or disorders associated with integrated stress response comprising administering to a subject in need a compound or a pharmaceutically acceptable salt, tautomer or stereoisomer thereof of claim 1 or a pharmaceutical composition thereof.

18. The method of claim 17, wherein the diseases or disorders are selected from the group consisting of leukodystrophies, intellectual disability syndrome, neurodegenerative diseases and disorders, neoplastic diseases, infectious diseases, inflammatory diseases, musculoskeletal diseases, metabolic diseases, ocular diseases, organ fibrosis, chronic and acute diseases of the liver, chronic and acute diseases of the lung, chronic and acute diseases of the kidney, myocardial infarction, cardiovascular disease, arrhythmias, atherosclerosis, spinal cord injury, ischemic stroke, and neuropathic pain.

* * * * *